(12) United States Patent
Loushin

(10) Patent No.: US 9,895,257 B2
(45) Date of Patent: Feb. 20, 2018

(54) GAS ALTERING CONVECTIVE THERMOREGULATION BLANKET

(76) Inventor: Michael K. H. Loushin, Shoreview, MN (US)

(*) Notice: Subject to any disclaimer, the term of this patent is extended or adjusted under 35 U.S.C. 154(b) by 1266 days.

(21) Appl. No.: 13/636,947

(22) PCT Filed: Mar. 22, 2011

(86) PCT No.: PCT/US2011/029385
§ 371 (c)(1),
(2), (4) Date: Oct. 30, 2012

(87) PCT Pub. No.: WO2011/119581
PCT Pub. Date: Sep. 29, 2011

(65) Prior Publication Data
US 2013/0041438 A1    Feb. 14, 2013
US 2016/0256314 A9    Sep. 8, 2016

Related U.S. Application Data

(60) Provisional application No. 61/316,532, filed on Mar. 23, 2010.

(51) Int. Cl.
*A61F 7/08* (2006.01)
*A61F 7/00* (2006.01)

(52) U.S. Cl.
CPC ...... *A61F 7/0097* (2013.01); *A61F 2007/006* (2013.01); *A61F 2007/0091* (2013.01)

(58) Field of Classification Search
CPC .............. A61F 2007/0054–2007/0057; A61F 2007/006; A61F 2007/0063; A61F 2007/0064
See application file for complete search history.

(56) References Cited

U.S. PATENT DOCUMENTS

| 2,093,834 A | * | 9/1937 | Gaugler | A41D 13/0053 126/204 |
| 4,391,009 A | * | 7/1983 | Schild | A61G 7/05776 297/180.11 |

(Continued)

FOREIGN PATENT DOCUMENTS

CH    266060    1/1950

OTHER PUBLICATIONS

Search Report and Written Opinion dated Sep. 12, 2011 for International Application No. PCT/US2011/029385, filed Mar. 22, 2011, 15 pages.

(Continued)

*Primary Examiner* — Ronald Hupczey, Jr.
(74) *Attorney, Agent, or Firm* — Leanne Taveggia Farrell; Westman, Champlin & Koehler, P.A.

(57) ABSTRACT

A convective thermoregulation blanket (204) includes an exterior surface (220), a plurality of interconnected distribution channels (940, 941) and a first inlet opening (1244). A portion of the exterior surface is configured to be in contact with a patient. The interconnected distribution channels are located internal to the convective thermoregulation blanket and include a primary distribution channel (940) having an interior surface. The first inlet opening extends between the exterior surface of the convective thermoregulation blanket and the interior surface of the primary distribution channel to deliver thermal regulated convective air into the primary distribution channel. At least a portion of the primary distribution channel includes a filter material. The filter material filters unfiltered thermal regulated convective air in the primary distribution channel and provides the remaining plurality of distribution channels with filtered thermal regulated convective air.

19 Claims, 15 Drawing Sheets

(56) References Cited

U.S. PATENT DOCUMENTS

| | | | |
|---|---|---|---|
| 4,777,802 A * | 10/1988 | Feher | A47G 9/0215 |
| | | | 5/423 |
| 4,888,958 A | 12/1989 | Ella | |
| 5,300,102 A | 4/1994 | Augustine et al. | |
| 5,304,213 A * | 4/1994 | Berke | A47G 9/0215 |
| | | | 607/104 |
| 5,305,483 A * | 4/1994 | Watkins | A47D 15/001 |
| | | | 128/202.18 |
| 5,876,428 A | 3/1999 | Van Duren | |
| 5,941,907 A | 8/1999 | Augustine | |
| 6,261,332 B1 * | 7/2001 | Richard | B01D 46/0023 |
| | | | 55/385.1 |
| 7,550,000 B2 | 6/2009 | Frey | |
| 8,414,671 B2 * | 4/2013 | Augustine | A47C 21/044 |
| | | | 128/205.12 |
| 9,095,803 B2 * | 8/2015 | Augustine | A61M 16/0875 |
| 2006/0271134 A1 * | 11/2006 | Frey | A61F 7/02 |
| | | | 607/104 |
| 2007/0244533 A1 | 10/2007 | Pierre et al. | |
| 2008/0307970 A1 | 12/2008 | Augustine et al. | |
| 2008/0308106 A1 | 12/2008 | Augustine et al. | |
| 2009/0223368 A1 | 9/2009 | Augustine et al. | |

OTHER PUBLICATIONS

Communication dated Jul. 26, 2013 for European Application No. 11712398.4 filed Oct. 2, 2012, 4 pages.

* cited by examiner

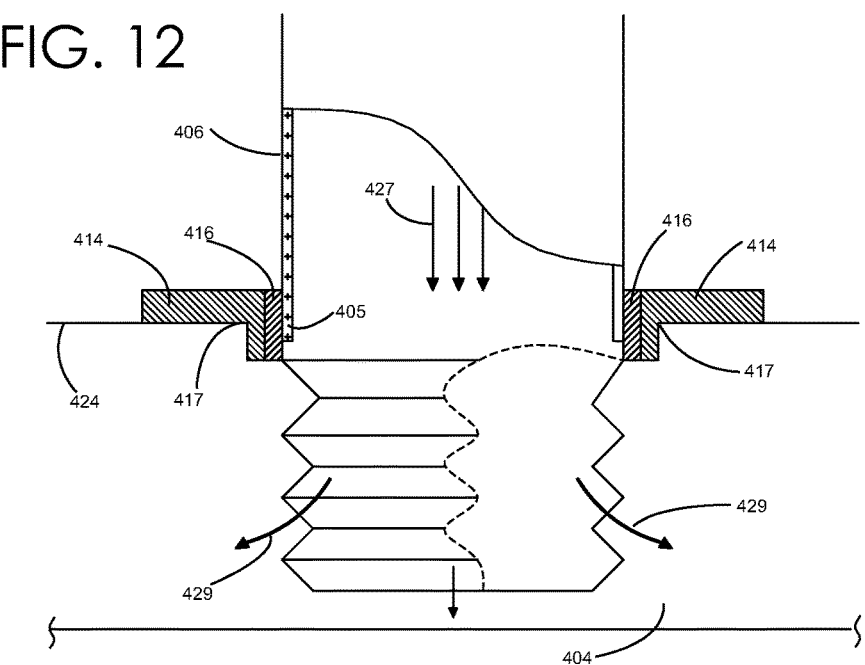
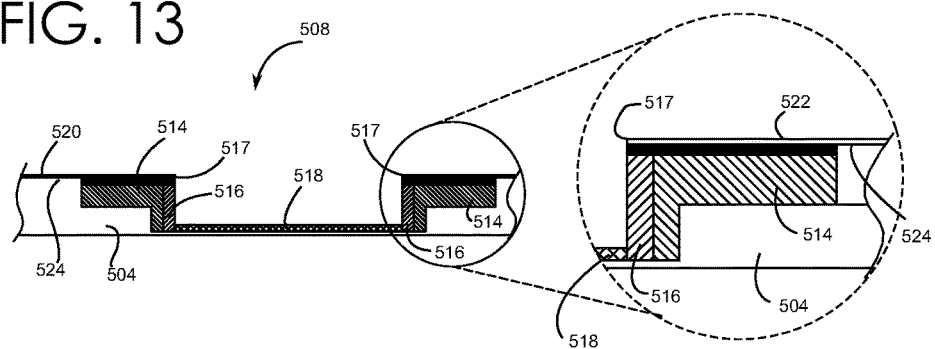
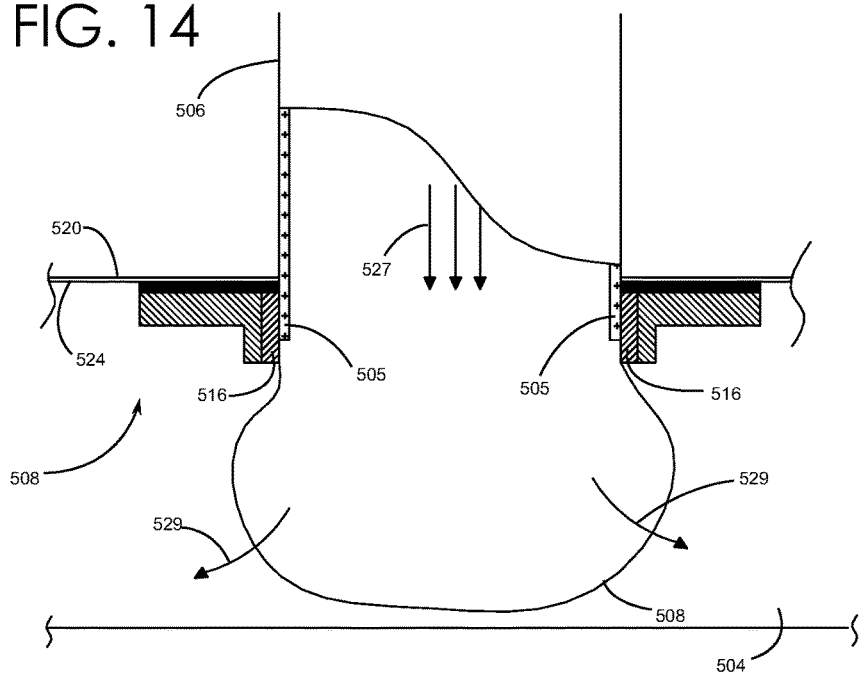

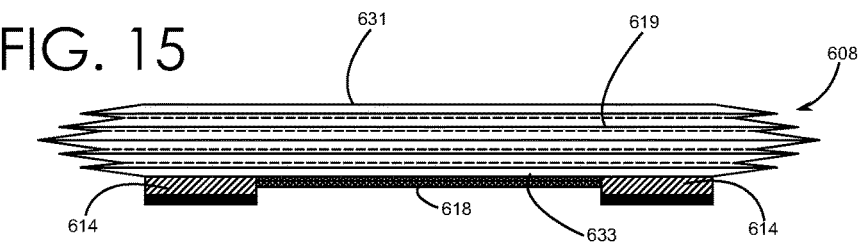
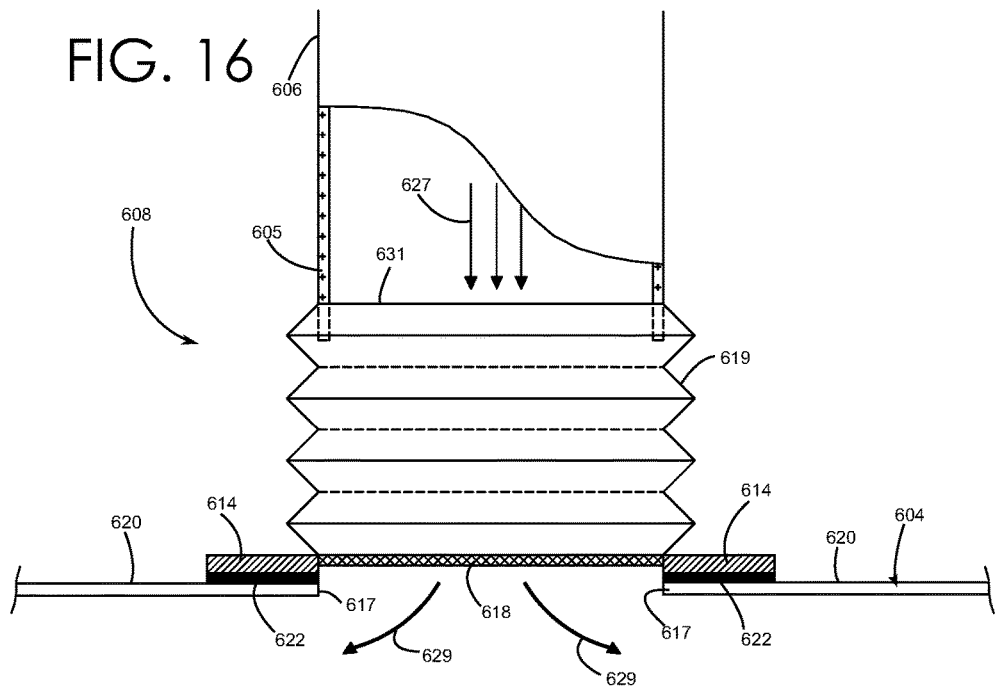
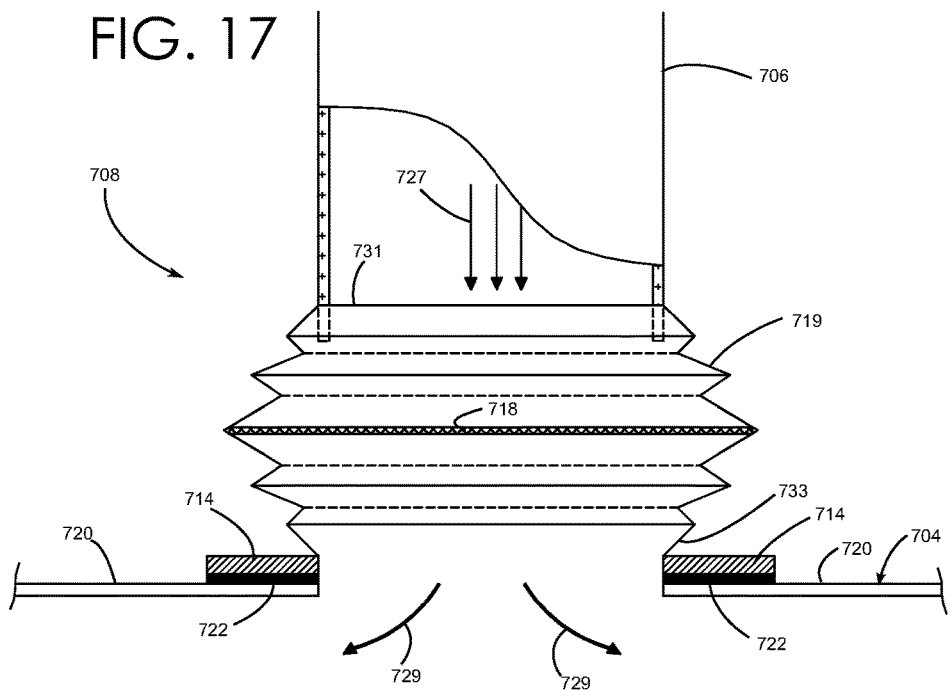

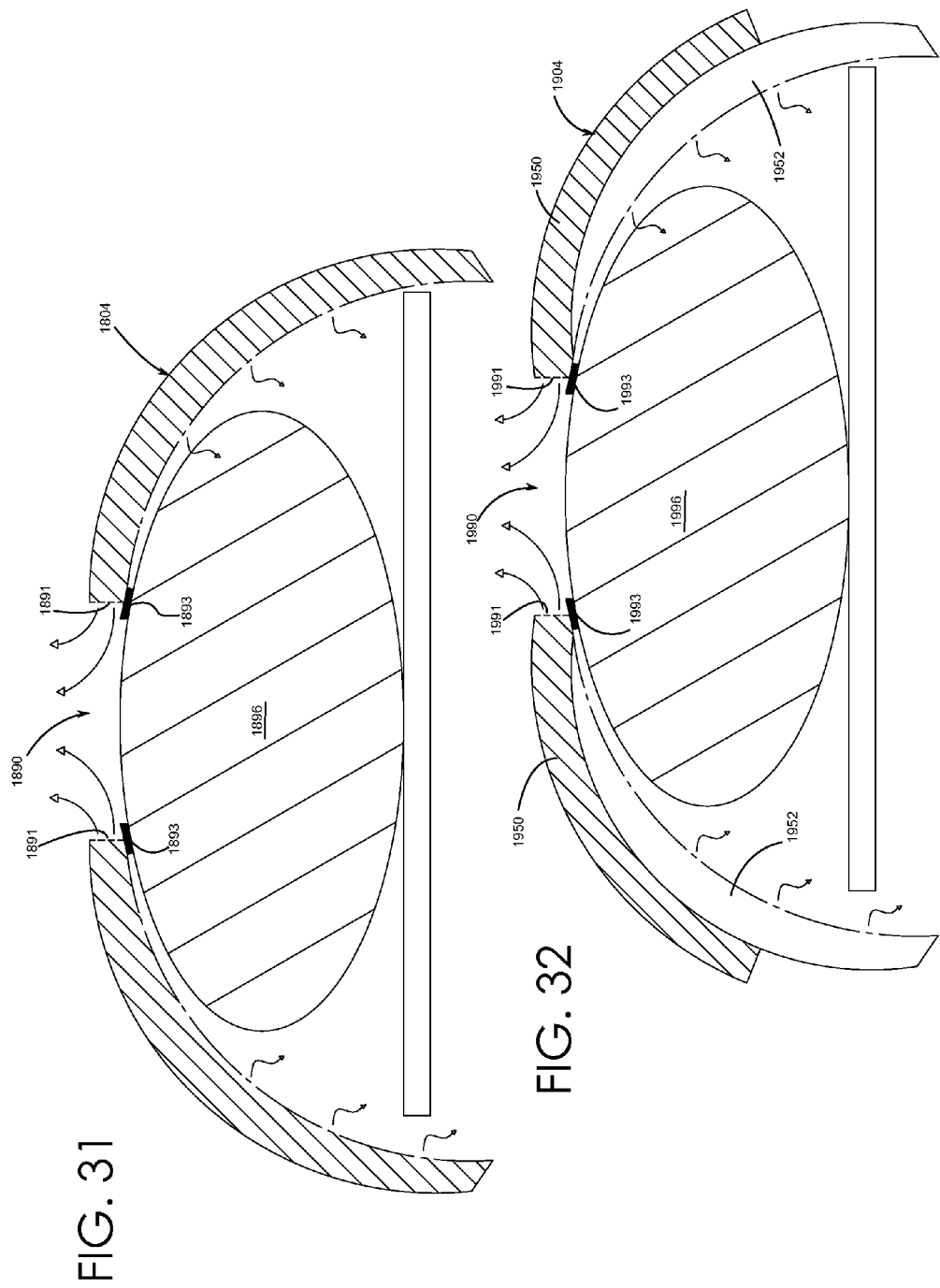

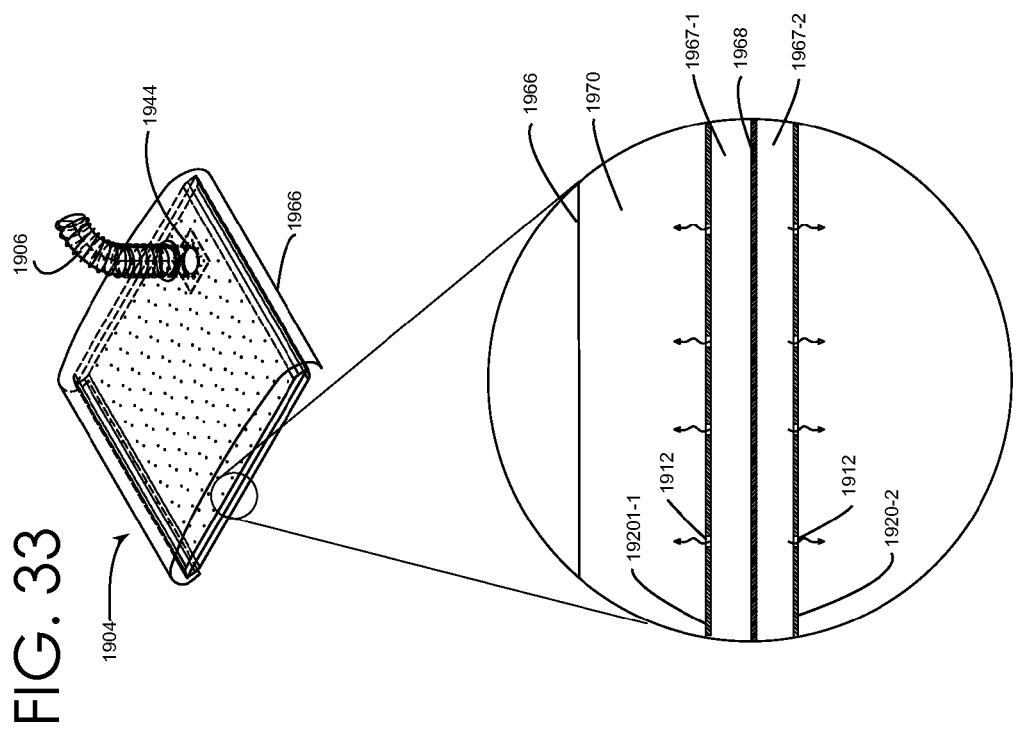

GAS ALTERING CONVECTIVE THERMOREGULATION BLANKET

CROSS-REFERENCE TO RELATED APPLICATION

This Application is a Section 371 National Stage Application of International Application No. PCT/US2011/029385, filed Mar. 22, 2011 and published as WO2011/119581 on Sep. 29, 2011, in English, the contents of which are hereby incorporated by reference in their entirety. The present application also claims the benefit of U.S. provisional patent application Ser. No. 61/316,532, filed Mar. 23, 2010.

BACKGROUND

During medical procedures, a patient lays on, is covered by or surrounded by a warming blanket. The temperature of the patient is regulated using the blanket in combination with a forced-air blower system. The blower system feeds air into a port in the blanket and the blanket disperses warm air through perforations in the blanket surface.

SUMMARY

A convective thermoregulation blanket includes an exterior surface, a plurality of interconnected distribution channels and a first inlet opening. A portion of the exterior surface is configured to be in contact with a patient. The interconnected distribution channels are located internal to the convective thermoregulation blanket and include a primary distribution channel having an interior surface. The first inlet opening extends between the exterior surface of the convective thermoregulation blanket and the interior surface of the primary distribution channel to deliver thermal regulated convective air into the primary distribution channel. At least a portion of the primary distribution channel includes a filter material. The filter material filters thermal regulated convective air in the primary distribution channel and provides the remaining plurality of distribution channels with filtered thermal regulated convective air.

Alternatively, the filter material is provided at the first inlet opening in the form of a filtration device. The filtration device includes a support body having a first surface, an opposing second surface and an aperture extending between the first surface and the second surface. The aperture includes an inwardly facing surface that defines a distance between the first and second surfaces of the support body. A sealing component is coupled to the support body and is configured to seal a distal end of a hose containing a supply of airflow with an inlet opening in the convective thermoregulation blanket. A filter element is coupled to the support body and extends across the aperture in the support body and the first inlet opening in the thermoregulation blanket. The filter element configured to filter harmful airborne contaminants in the supply of airflow in the hose.

Embodiments provide a gas altering convective thermoregulation blanket having an inlet port configured to receive an anesthesia gas circuit or hose of a blower/fan unit. The inlet port includes a support body, a gasket or other sealing mechanism and a filter element for filtering out harmful particulate matter to provide a thermoregulated clean or sterile environment for a surgical site, incision, wound, surgical tray/table, surgical instruments, implants, or patient. The system can be controlled for airflow, air filtration, gas concentration, gases, humidity and/or temperature.

BRIEF DESCRIPTION OF THE DRAWINGS

FIG. 12 is a sectional view of the filtration device illustrated in FIG. 11 as a supply of convective air is delivered into the thermoregulation blanket.

FIG. 13 is a sectional view of a filtration device for a convective thermoregulation blanket under another embodiment.

FIG. 14 is a sectional view of the filtration device illustrated in FIG. 13 as a supply of convective air is delivered into the thermoregulation blanket.

FIG. 15 is a sectional view of a filtration device for a convective thermoregulation blanket under another embodiment.

FIG. 16 is a sectional view of the filtration device illustrated in FIG. 15 as a supply of convective air is delivered into the thermoregulation blanket.

FIG. 17 is a sectional view of a filtration device for a convective thermoregulation blanket under another embodiment.

FIGS. 23-1, 23-2 and 23-3 illustrate diagrammatic top views of further embodiments of a convective thermoregulation blanket.

FIGS. 29-1 through 29-3 illustrate perspective views of a convective thermoregulation blanket under another embodiment.

FIG. 31 illustrates a diagrammatic section view of another embodiment of a patient and thermoregulation blanket.

FIG. 32 illustrates a diagrammatic section view of yet another embodiment of a patient and thermoregulation blanket.

FIG. 33 illustrates a diagrammatic view of another embodiment of a convective thermoregulation blanket.

DETAILED DESCRIPTION

Figure 1:
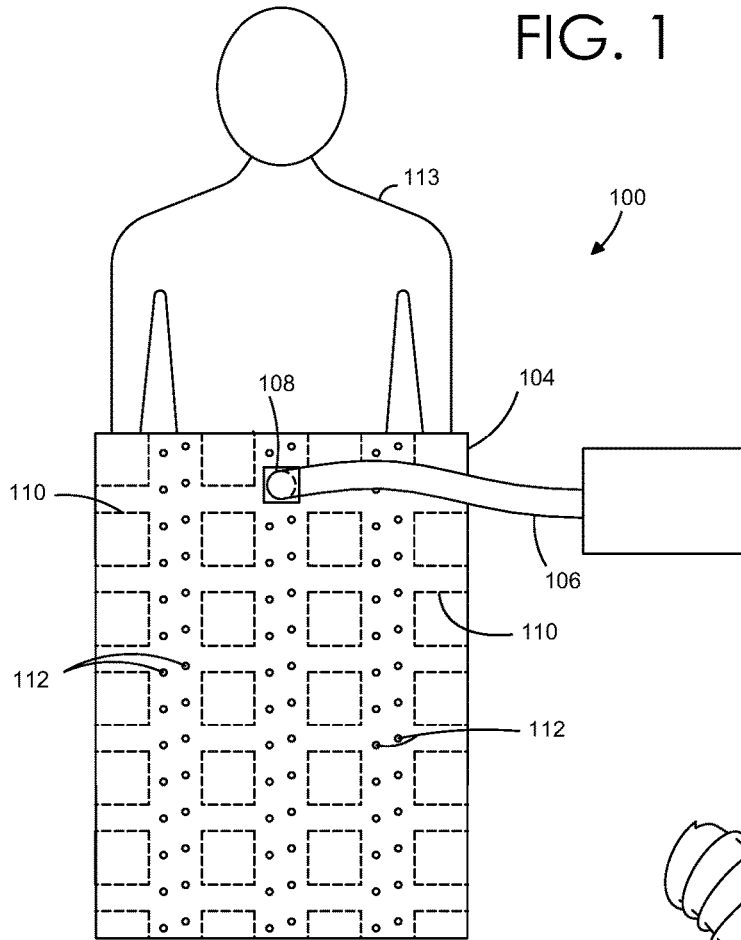
FIG. 1 is a schematic diagram of a convective thermoregulation blanket.

Embodiments of the disclosure provide a clean or sterile environment using a convective thermoregulation system by including filtration components attached to or incorporated into a convective blanket. By filtering airborne microbes or particles at the blanket level, there is a decrease in the risk of infections caused by local or airborne contamination. In addition, the blanket, in combination with the filtration components, for example, a high efficiency particulate air filter, can create a clean or sterile environment of airflow that will allow the alteration of oxygen, temperature, humidity, and/or gas/air concentration on or near a clean or sterile surgical environment. The ability to blow filtered clean or sterile air on or near a clean or sterile environment with varying gas concentrations, humidity, or temperature on or near a surgical site or patient will significantly decrease the risk of contamination of surgical environment, surgical site infections, or operating room or surgical site fires.

Currently available convective blankets and thermoregulation systems are designed to keep blowing air away from a surgical site due to risk of contamination. Directly blowing air on or around a surgical site is avoided with current convective systems since the air blown into the blanket that exits the blanket through the outlet opening(s) may contain harmful airborne particulate matter such as dust, microbes, human cells or cell components, respiratory droplets, and any particulate matter generated by the blower unit or from ambient air. Additionally, airborne contamination can be introduced into the clean or sterile environment by blowing contaminated air on or near the clean or sterile field by alteration of airflow or gas property such as density, or differences in air temperatures. For example, airflow can be disrupted by alteration of airflow, by difference in temperatures of air or gas, vented or exhaust air, or excess or waste heat from a convective blower, blanket, or a thermoregulation unit. For example, warm air from the blower unit or blanket can travel along the patient or drape, exit the drape near the floor, and the warmer air such as exhaust air or waste heat can rise carrying with it contaminants from or near the floor along with particulates from dust, skin, cells or cell particles, droplets, surgical drape, blanket, blower, or operating room personnel near the sterile surgical environment. The airborne particulates or microbes can travel or be carried by airflow, heat currents or warm air and settle into a clean or sterile surgical environment, incision, or wound. Contamination by airborne matter or other airborne mobilized contaminates can contact a clean or sterile environment, and therefore increase the risk of contamination or infection of surgical incision/wound, surgical drape, surgical instruments, instrument tray, or implants. By providing filtered clean or sterile or particulate free air on or around a sterile surgical environment, incision, or wound, the contaminated or particulate-laden air from ambient, vented or exhaust air, or excess or waste heat is displaced, diluted, altered, modified, or regulated from the surrounding clean or sterile environment thus decreasing the risk of surgical site infection or contamination to surgical instruments, trays/tables, or implants.

Additionally, the ability to provide filtered clean or sterile air on or near a surgical environment can reduce the risk of operating room fires. During certain medical procedures, the risk of an operating room fire is increased especially when higher concentrations of oxygen (at or above ambient) are provided to a spontaneously, assisted, or mechanically breathing patient by a supplemental oxygen source via blow-by, facemask, nasal cannula, endotracheal tube or airway device, flexible or rigid bronchoscope, venturi, or jet ventilation creating an oxygen rich environment on or near a patient or clean or sterile surgical environment. Oxygen or other flammable or combustible gases from a source, such as vapor or liquid from surgical prep solution, can be entrapped on or near the surgical environment or patient, especially when surgical drapes are utilized to enclose a clean or sterile surgical environment. The higher concentration of oxygen or flammable gas(es) can be diluted, displaced, altered, modified, or regulated by blowing filtered clean or sterile air or gas such as helium, nitrogen, or carbon dioxide that is less flammable or nonflammable to reduce or eliminate surgical fire risks.

By providing filtration components attached to or incorporated into a convective thermoregulation blanket utilizing varying gases that are, for example, low in oxygen, inert, or noncombustible such as ambient air, nitrogen, carbon dioxide, or helium, airflow exiting the blanket can dilute or displace (i.e., wash out) gas(es) that create or support combustion such as flammable gases, accelerants, or oxidizers. The filtration components attached to or incorporated in the blanket can filter out harmful microbes and particles, and air can exit the blanket through the array of outlet openings to displace or dilute the higher concentration of oxygen and flammable gases, thereby altering the oxygen rich environment around the patient and reducing the risk of operating room or surgical fires.

FIG. 1 illustrates a schematic diagram of a convective thermoregulation system 100 including a blower unit 102 and a convective thermoregulation blanket 104. Blower unit 102 includes components for pulling in ambient room air, warming or cooling the air with, for example a heater or refrigerant, and blowing the conditioned air through a hose 106 into convective thermoregulation blanket 104 at an inlet port 108. In addition, blower unit 102 can include components for controlling the humidity of output air. Internal channels or chambers 110 in convective thermoregulation blanket 104 distribute air throughout the blanket and exits onto the patient at outlet openings 112. Although FIG. 1 illustrates convective thermoregulation blanket 104 as having a plurality of outlet openings 112 distributed along each of the internal channels or chambers 110, it should be realized that other types of outlet openings 110 are possible. For example, convective thermoregulation blanket 104 can have a single outlet opening or an outlet opening for each channel or chamber. In addition, while outlet openings 112 are illustrated as opening to the top of the blanket 104, outlet openings 112 can be located on either or the bottom and top of the blanket depending on whether the patient is laying underneath or on top of blanket 104.

As illustrated, convective thermoregulation blanket 104 is placed on or under a patient 113 to warm or cool desired areas of the patient. Of the illustrated convective thermoregulation system 100, convective thermoregulation blanket 104 is disposable. In particular, the convective thermoregulation blanket can be made of a top layer of plastic sheeting and a bottom layer of paper or other woven or non-woven material. While blanket 104 is disposable, hose 106 and the blower unit 102 are reused for other patients. Therefore, the end of hose 106 is inserted into hose inlet ports of different convective thermoregulation blankets for different patients.

Figure 2:
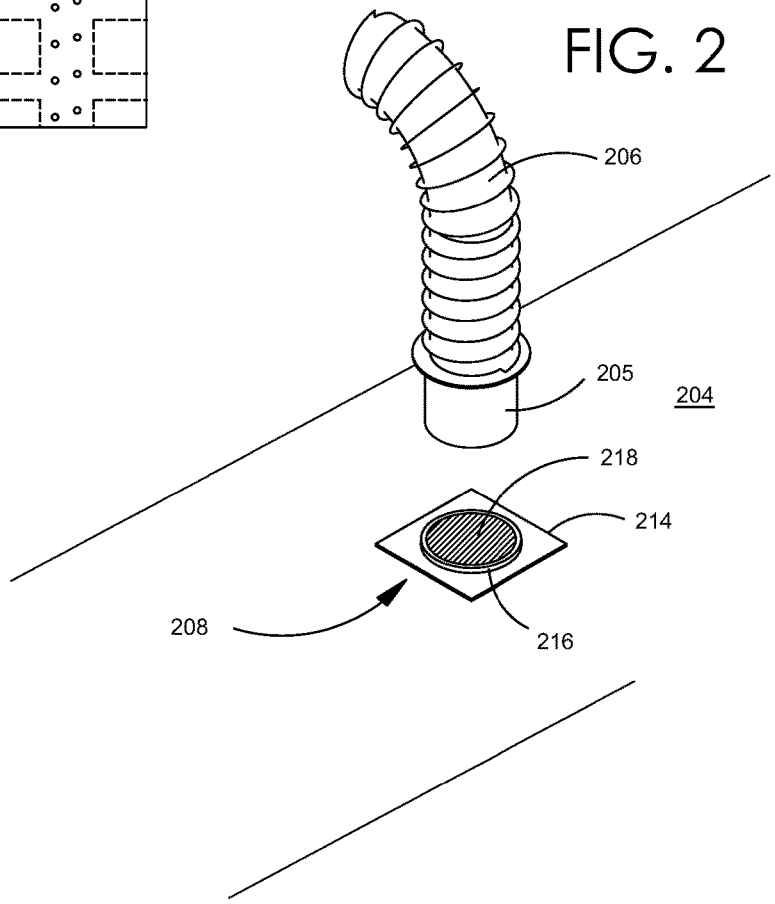
FIG. 2 is a perspective view of a filtration device for a convective thermoregulation blanket under one embodiment.
Figure 3:
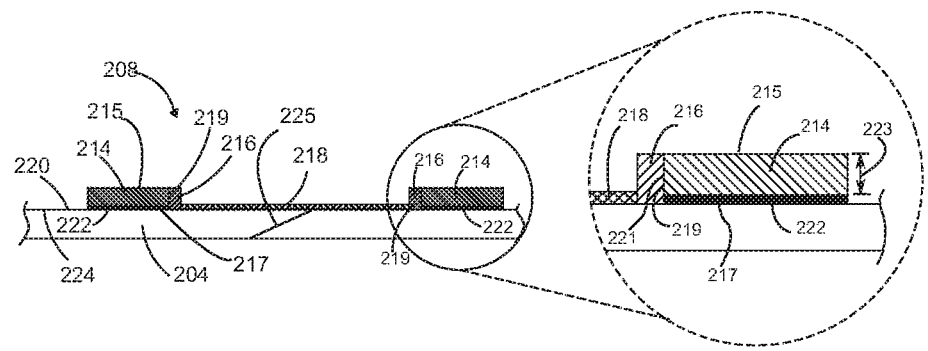
FIG. 3 is a sectional view of the filtration device illustrated in FIG. 2.

FIG. 2 is a top plan view of a filtration device 208 coupled to a convective thermoregulation blanket 204 under one embodiment, while FIG. 3 is a sectional view of filtration device 208 and blanket 204 of FIG. 2. Filtration device 208 is configured to receive a hose 206 connected to a blower unit or forced-air blower system.

Filtration device 208 includes a support body 214, a gasket or sealing component 216 and a filter element 218. As illustrated in detail in FIG. 3, support body 214 includes a first surface 215, an opposing second surface 217 and an aperture 219 extending between the first 215 and second 217 surfaces. Aperture 219 has an inwardly facing surface 221 that defines a distance 223 between the first 215 and second 217 surfaces. Support body 214 supports gasket 216 and filter element 218, which are all coupled together by, for example, lamination, adherence or other type of attachment means. As illustrated in FIG. 3, support body 214 of filtration device 208 can be attached to an exterior surface 220 of convective thermoregulation blanket 204 by an adhesive 222. It should be realized that other means are possible, such as by lamination.

Gasket or sealing component 216 is configured to seal a distal end 205 of hose 206 with an inlet opening in thermoregulation blanket 204. Hose 206 contains a supply of convective airflow. In one embodiment, filtration device 208 can be assembled together and then fastened or affixed to exterior surface 220 of convective thermoregulation blanket 204 in a location where the blanket has been nicked with a slit 225 that extends between exterior surface 220 and an interior surface 224 of thermoregulation blanket 204. Upon sealing the distal end 205 of hose 206 to gasket or sealing component 216, slit 225 is widened to become the inlet opening in which the convective airflow 227 (FIG. 4) supplied from hose 206 is delivered into thermoregulation blanket 204. Filter element 218 is coupled to inwardly facing surface 221 and extends across aperture 219 in support body 214.

Figure 4:
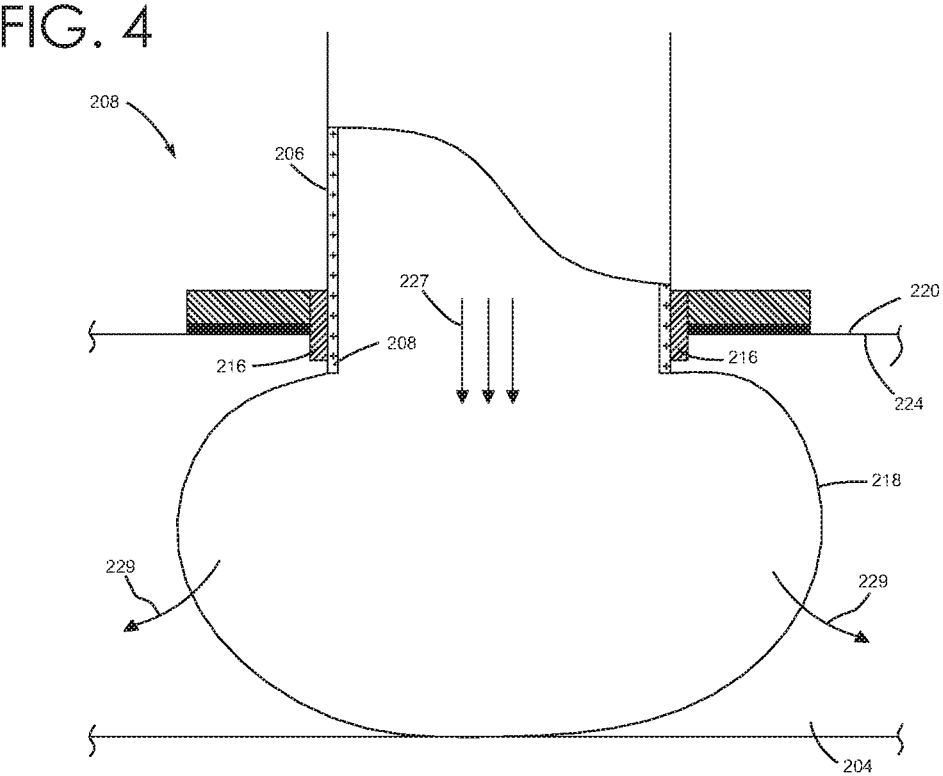
FIG. 4 is a sectional view of the filtration device illustrated in FIG. 2 as a supply of convective air is delivered into the thermoregulation blanket.

As illustrated in the sectional view of FIG. 4, filtration device 208 receives a distal end 205 of hose 206, which pushes filter element 218 through and into the interior of the blanket at the location of the slit 225 or inlet opening. After gasket 216 seals hose 206 to convective thermoregulation blanket 204, the supply of convective airflow 227 from hose 206 is delivered into the convective thermoregulation blanket and inflates filter element 218 within the blanket. Filter element 218 filters harmful airborne contaminants flowing from the supply of airflow 227 in hose 206 before clean air 229 is distributed throughout the channels or chambers of the blanket 204.

Figure 5:
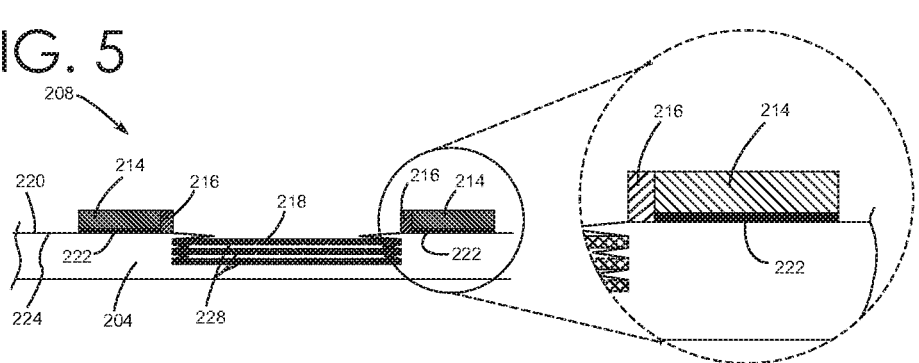
FIG. 5 is a sectional view of an alternative embodiment of the filtration device illustrated in FIG. 2.
Figure 6:
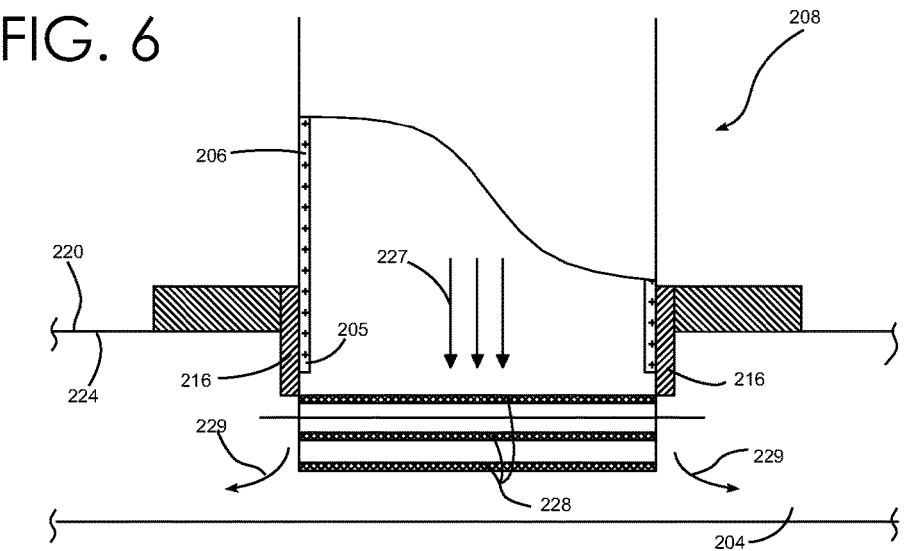
FIG. 6 is a sectional view of the alternative filtration device illustrated in FIG. 5 as a supply of convective air is delivered into the thermoregulation blanket.

FIGS. 5 and 6 are sectional views of an alternative embodiment of filtration device 208 coupled to a convective thermoregulation blanket 204. Like the embodiment illustrated in FIG. 3, alternative filtration device 208 includes support body 214, gasket or sealing component 216 and filter element 218. Support body 214 supports gasket 216 and filter element 218, which are all coupled together by, for example, lamination, adherence or other type of attachment means. In addition, support body 214 of filtration device 208 is attached to exterior surface 220 of convective thermoregulation blanket 204 by an adhesive 222.

In FIG. 5, filter element 218 includes a plurality of filters 228 stacked together in layers and spaced apart from each other rather than the single filter shown in FIG. 3. More particularly, FIG. 5 illustrates three filters. However, it should be realized that any number of filters can be used. Each of the plurality of filters 228, for example, can be a different type of filter that filters different size particles. Although not specifically illustrated in FIG. 5, filter element 218 can be positioned at different points relative to the support body 214 and gasket 216. In FIG. 5, filter element 218 is positioned below support body 214. However, filter element 218 can be positioned above support body 214 or along the same plane as the support body.

As illustrated in FIG. 6, filtration device 208 receives a distal end 205 of hose 206, which unfolds filter element 218 to push filters 228 through and into the interior of the blanket 204 at the location of an inlet opening. After gasket 216 seals hose 206 to convective thermoregulation blanket 204, the supply of convective airflow 227 from hose 206 is delivered into the convective thermoregulation blanket and expands filters 228 into the interior of the blanket 204. Filters 228 filter harmful airborne contaminants flowing from the supply of airflow 227 in hose 206 before clean air 229 is distributed throughout the channels or chambers of the blanket 204. With filter element 218 being in the form of multiple layers of filters 228, the multiple filters 228 can more easily retain particles when the hose 206 is removed.

Figure 7:
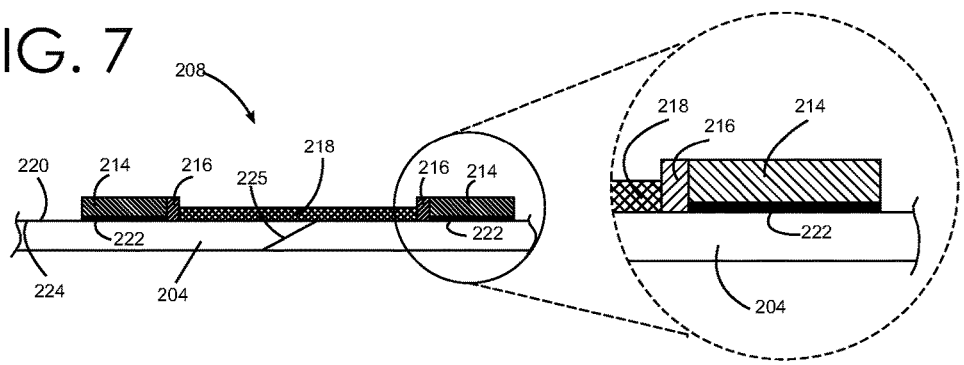
FIG. 7 is a sectional view of an alternative embodiment of the filtration device illustrated in FIG. 2.
Figure 8:
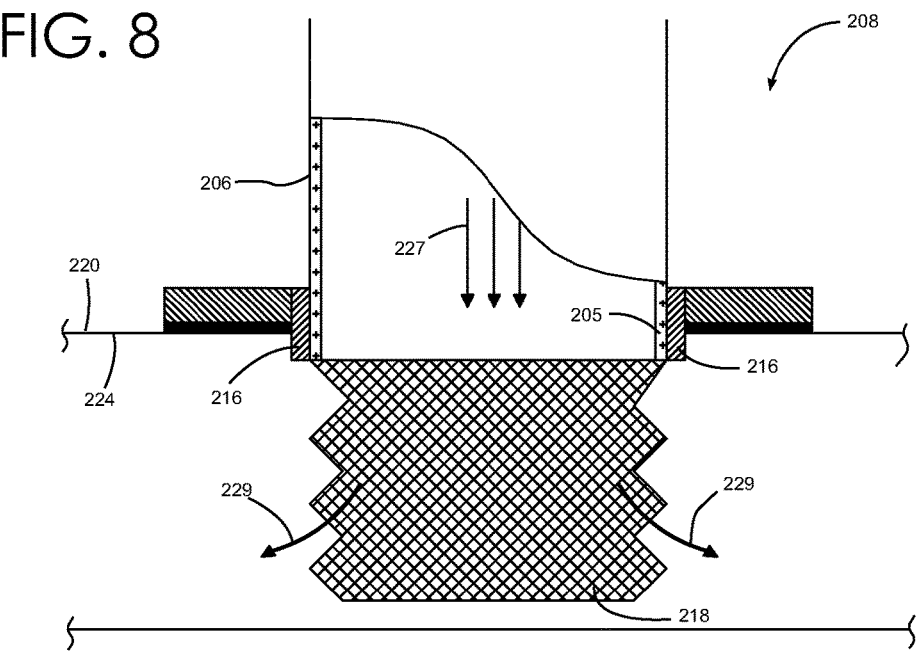
FIG. 8 is a sectional view of the alternative filtration device illustrated in FIG. 7 as a supply of convective air is delivered into the thermoregulation blanket.

FIGS. 7 and 8 are sectional views of an alternative embodiment of filtration device 208 coupled to a convective thermoregulation blanket 204. Like the embodiments illustrated in FIGS. 3-6, filtration device 208 includes support body 214, gasket or sealing component 216 and filter element 218. Support body 214 supports gasket 216 and filter element 218, which are all coupled together by, for example, lamination, adherence or other type of attachment means. In addition, support body 214 of filtration device 208 is attached to exterior surface 220 of convective thermoregulation blanket 204 by an adhesive 222. It should be realized that other means are possible, such as by lamination.

As illustrated in FIG. 8, filtration device 208 receives a distal end 205 of hose 206, which unfolds filter element 218 to push filter element 218 through and into the interior of the blanket 204 at the location of an inlet opening. In one embodiment, filter element 218 is an accordion style filter that can be compressed together in a flattened state when inlet port 208. However, it is also possible for filter element 218 to be a bag style filter that is placed between layers of a thermoregulation blanket 204. It should be realized that filter 1719 can be of varying length size depending on channel size and filtering capabilities. In addition, filter element 204 can be removable, resealable, reattachable and disposable.

Figure 9:
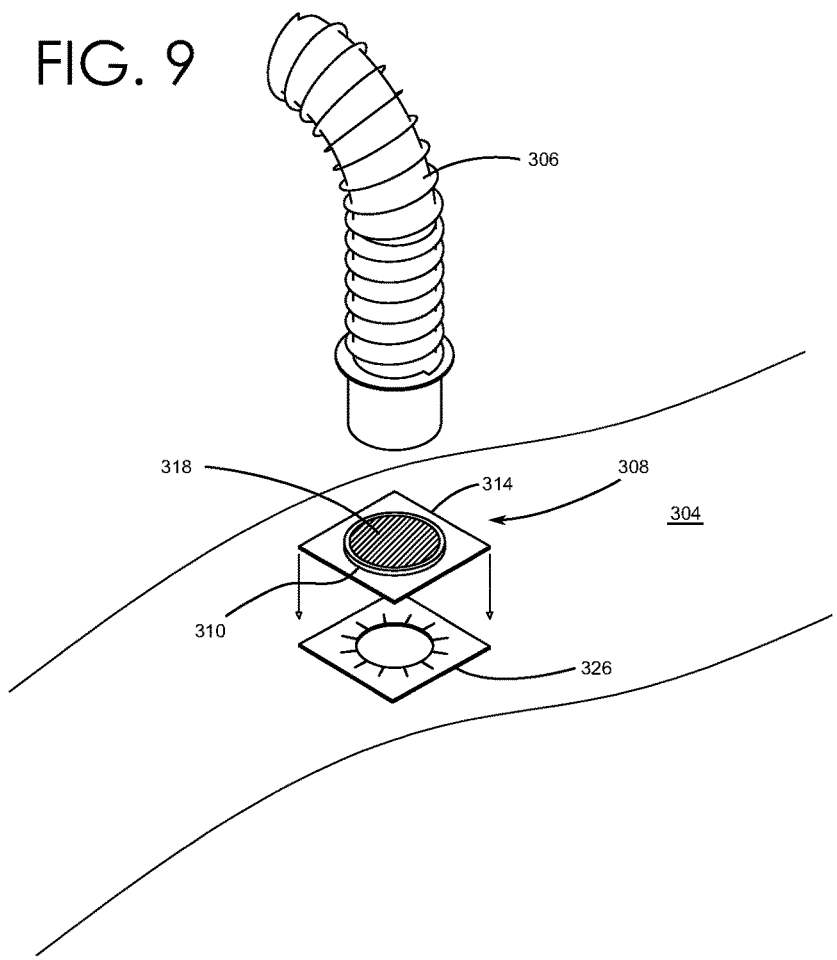
FIG. 9 is a perspective view of a filtration device for a convective thermoregulation blanket under another embodiment.
Figure 10:
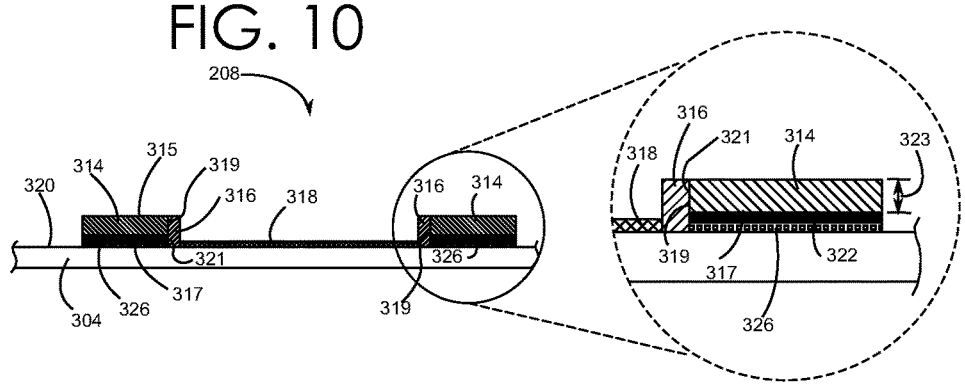
FIG. 10 is a sectional view of a filtration device illustrated in FIG. 9.

FIG. 9 is a top perspective view of a filtration device 308 coupled to a convective thermoregulation blanket 304 under one embodiment, while FIG. 10 is a sectional view of filtration device 308 and blanket 304 of FIG. 9. Filtration device 308 is configured to receive a hose 306 connected to a blower unit or forced-air blower system.

Filtration device 308 includes a support body 314, a gasket or sealing component 316 and a filter element 318. As illustrated in detail in FIG. 10, support body 314 includes a first surface 315, an opposing second surface 317 and an aperture 319 extending between the first 315 and second 317 surfaces. Aperture 319 has an inwardly facing surface 321 that defines a distance 323 between the first 315 and second 317 surfaces. Support body 314 supports gasket 316 and filter element 318 which are all coupled together by, for example, lamination, adherence or other type of attachment means. Instead of support body 314 being directly attached to an exterior surface 320 of a convective thermoregulation blanket 304 as illustrated in FIGS. 2-7, support body 314 is attached to a previously existing inlet port body 326 already attached to the exterior surface 320 of the convective thermoregulation blanket 304. Existing inlet port body 326 is attached to an exterior surface (such as exterior surface 320) by for example, adhesive 322. Other attachment means are possible, including lamination, adhesion or the like.

While FIGS. 9 and 10 illustrate a single filter element 318 that can expand into the interior of blanket 304, other embodiments of filter element 318 are possible. For example, filter element 318 can be a plurality of filters stacked together in layers and spaced apart from each other as illustrated in FIGS. 5 and 6 or filter element 318 can be an accordion style or bag style filter element as illustrated in FIGS. 7 and 8.

Figure 11:
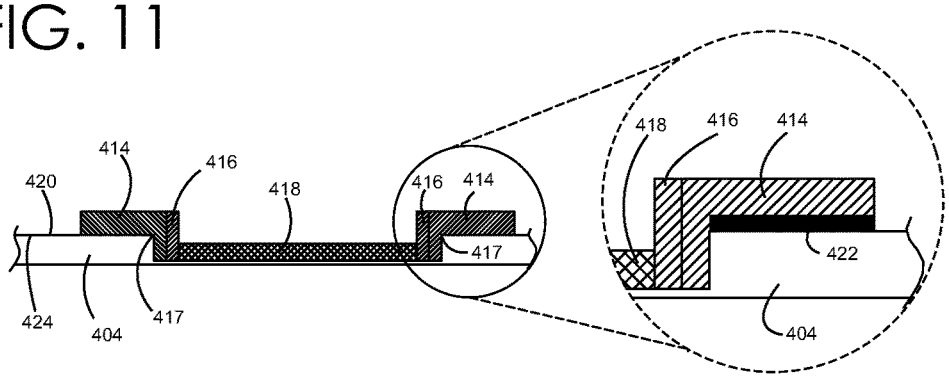
FIG. 11 is a sectional view of a filtration device for a convective thermoregulation blanket under another embodiment.

FIG. 11 is a sectional view of a filtration device 408. Filtration device 408 is a separate assembly structure from a convective thermoregulation blanket 404 and can be attached to a convective thermoregulation blanket 404 when the blanket is to be used. Filtration device 408 includes a support body 414, a gasket or sealing component 416 and a filter element 418. Support body 414 and gasket 416 are configured such that upon use, both components extend into the interior of a convective thermoregulation blanket through an opening 417 extending between the exterior surface 420 and the interior surface 424 of the blanket. More specifically, support body 414 is attached to an exterior surface 420 of a blanket using an adhesive 422. For example, adhesive 422 can be included with a backing material across its exposed surface. To use the filtration device 408, the backing can be removed and the adhesive 422 can fasten or affix the assembled structure of the support body 414, gasket 416 and filter element 418 to the convective thermoregulation blanket 404. Support body 414 supports gasket 416 and filter element 418 which are all coupled together by, for example, lamination, adherence or other type of attachment means.

Like the embodiment illustrated in FIG. 8, filter element 418 is an accordion style filter that can be compressed together in a flattened state (as illustrated in FIG. 11) when filtration device 408 is not coupled to a hose of a blower unit. Upon use, inlet port 408 is affixed to the exterior surface 420 of convective thermoregulation blanket 404 in a location where the blanket includes an inlet opening. However, and as illustrated in FIG. 12, support body 414 and gasket 416 protrude from exterior surface 422 and extend into the interior of the convective thermoregulation blanket 404 beyond an interior surface 424 and beyond opening 417 in blanket 404. Therefore and as illustrated in FIG. 12, filtration device 408 can receive a distal end 405 of a hose 406, which expands the accordion style filter element 418 through and into the interior of the blanket. After gasket 416 seals the hose to convective thermoregulation blanket 404, the supply of convective airflow 427 from hose 406 is delivered into the convective thermoregulation blanket and expands accordion filter 418 into the interior of the blanket 404. Filter 418 filters harmful airborne contaminants flowing from the supply of airflow 427 in hose 406 before clean air 429 is distributed throughout the channels or chambers of the blanket 404.

FIG. 13 is a sectional view of a filtration device 508 as inserted into a convective thermoregulation blanket 504. Filtration device 508 is a separate assembly structure from a convective thermoregulation blanket 504 and can be attached to an interior surface 524 of convective thermoregulation blanket 504.

Filtration device 508 includes a support body 514, a gasket or sealing component 516 and a filter element 518. Support body 514 and gasket 516 are configured such that upon use, both components are inserted through an inlet opening 517 located in convective thermoregulation blanket that extends between an exterior surface 520 and an interior surface 524 of the blanket. After filtration device 508 is inserted through inlet opening 517, support body 514 and gasket 516 are attached to interior surface 524 of blanket 504 using an adhesive 522. For example, adhesive 522 can be included with a backing material across its exposed surface. To use filtration device 508, the backing can be removed and the adhesive 522 can fasten or affix the assembled structure of the support body 514, gasket 516 and filter element 518 to the interior surface 524 of convective thermoregulation blanket 504. Support body 514 supports gasket 516 and filter element 518 which are all coupled together by, for example, lamination, adherence or other type of attachment means.

FIG. 14 illustrates exemplary filter element 518 as being a balloon style filter that can be compressed together in a flattened state (as illustrated in FIG. 13) when filtration device 508 is not being used. When filtration device 508 receives a distal end 505 of a hose 506 having a supply of convective air 527, the balloon style filter element 518 expands into the interior of the blanket. After gasket 516 seals the hose 506, air 527 is delivered into the convective thermoregulation blanket 504. Filter element 518 filters harmful airborne contaminants flowing from the supply of airflow 527 in hose 506 before clean air 529 is distributed throughout the channels or chambers of the blanket 504.

FIG. 15 is a sectional view of a filtration device 608 under yet another embodiment. Filtration device 608 can be a separate assembly structure that can be attached to a convective thermoregulation blanket when an over-the-body or under-the-body blanket is to be used. In the alternative, filtration device 608 can be incorporated with a convective thermoregulation blanket or any reusable or disposable air distribution blanket upon manufacture. Filtration device 608 includes a support body 614, a filter element 618 and a flexible ducting element 619 attached to the support body 614. Flexible ducting element 619 includes openings on two opposing ends. In particular, flexible ducting element 619 includes a proximal end 631 and a distal end 633. At the distal end 633, ducting element 619 is attached to support body 614, which is also supports filter element 618. The proximal end 631 of ducting element 619 is configured to receive a hose having a supply of convective air.

FIG. 16 is a sectional view of filtration device 608 as attached to convective thermoregulation blanket 604. As illustrated in FIG. 16, support body 614 of filtration device 608 can be attached to an exterior surface 620 of convective thermoregulation blanket 604 by an adhesive 622. It should be realized that other means are possible. In one embodiment, filtration device 608 is attached to the exterior surface 620 of blanket 604 at a location of an inlet opening 617 in the blanket. In another embodiment, filtration device 608 is attached to the exterior surface 620 of blanket 604 when the blanket is to be used. In this embodiment, for example, adhesive 622 can be included with a backing material across its exposed surface. Upon use of filtration device 608, the backing can be removed and the adhesive 622 fastens or affixes the assembled structure of the support body 614, filter element 618 and flexible ducting element 619 to convective thermoregulation blanket 604.

Therefore and as illustrated FIG. 16, flexible ducting element 619 of filtration device 608 can receive a distal end 605 of a hose 606 at its proximal end 631. Proximal end 631 seals ducting element 619 to the hose 606. After sealed, the supply of convective air 627 is delivered (from a blower unit) through the ducting element 619 and filter element 618 and into the convective thermoregulation blanket 604. Filter element 618 filters harmful airborne contaminants flowing from the supply of airflow 627 in hose 606 before clean air 629 is distributed throughout the channels or chambers of the blanket.

FIG. 17 is a sectional view of a filtration device 708 under yet another embodiment. Like filtration device 608, filtration device 708 is a separate assembly structure that can be attached to a convective thermoregulation blanket 704 when the blanket is to be used. In the alternative, filtration device 708 can be incorporated with a convective thermoregulation blanket 704 upon manufacture. Also like filtration device 608, filtration device 708 includes a support body 714, a filter element 718 and a flexible ducting element 719 attached to the support body 714. Flexible ducting element 719 has an accordion-type shape and includes openings on two opposing ends. At the distal end 733, ducting element 719 is attached to support body 714. At the proximal end 731, ducting element 719 is configured to receive a hose 706. Proximal end 731 seals ducting element 719 to the hose 706. After sealed, the supply of convective air 727 is delivered (from a blower unit) through the ducting element 719 and filter element 718 and into the convective thermoregulation blanket 704. Filter element 718 filters harmful airborne contaminants flowing from the supply of airflow 727 in hose 706 before clean air 729 is distributed throughout the channels or chambers of the blanket 704. Unlike filtration device 608, filter element 718 of filtration device 708 is supported by the walls of the flexible ducting element 719. As illustrated in FIG. 17, filter element 718 is positioned at a midpoint of the ducting element 719. However, other positions are possible.

Figure 18:
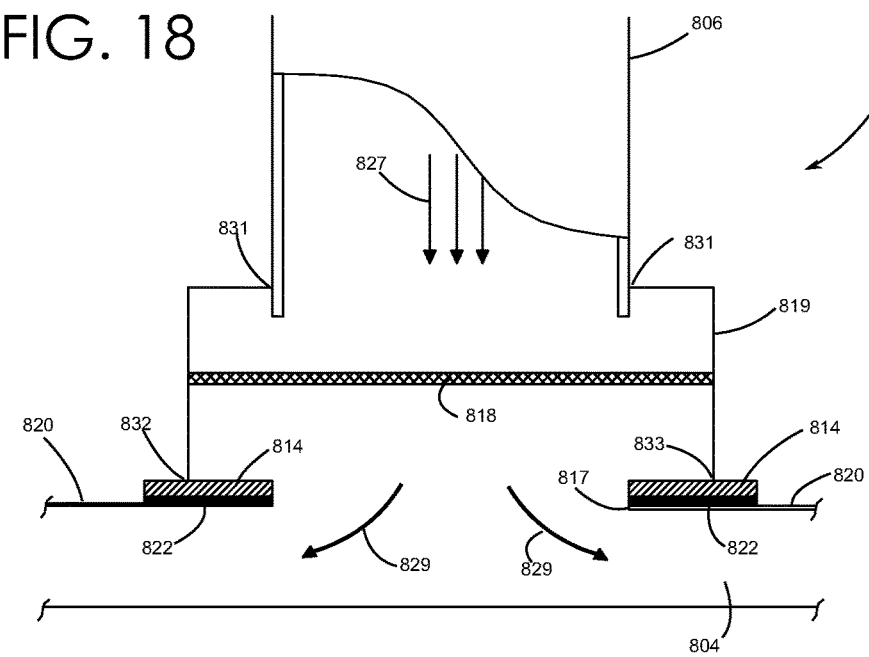
FIG. 18 is a sectional view of an alternative embodiment of the filtration device illustrated in FIG. 17.

FIG. 18 a sectional view of a filtration device 808 for a convective thermoregulation blanket 804 under yet another embodiment. Like filtration device 708, filtration device 808 can be a separate assembly structure that can be attached to a convective thermoregulation blanket 804 when the blanket is to be used. In the alternative, filtration device 808 can be incorporated with a convective thermoregulation blanket upon manufacture. Also, like filtration device 708, filtration device 808 includes a support body 814, a filter element 818 and a flexible ducting element 819 attached to the support body 814. Flexible ducting element 819 has a compressible box-type shape and includes openings on two opposing ends. At the distal end 833, ducting element 819 is attached to support body 814. At proximal end 831, ducting element 819 is configured to receive a hose 806. Proximal end 831 seals ducting element 819 to the hose 806. After sealed, the supply of convective air 827 is delivered (from a blower unit) through the ducting element 819 and filter element 818 and into the convective thermoregulation blanket 804. Filter element 818 filters harmful airborne contaminants flowing from the supply of airflow 827 in hose 806 before clean air 829 is distributed throughout the channels or chambers of the blanket 804. Like filtration device 708, filter element 818 is supported by the walls of the flexible ducting element 819. As illustrated in FIG. 18, filter element 818 is positioned at a midpoint of the ducting element 819. However, other positions are possible.

Support body 814 of filtration device 808 can be attached to an exterior surface 820 of convective thermoregulation blanket 804 by an adhesive 822. It should be realized that other means are possible. In one embodiment, filtration device 808 is attached to the exterior surface 820 of blanket 804 at a location of an inlet opening 817 in the blanket. In another embodiment, filtration device 808 is attached to the exterior surface 820 of blanket 804 when the blanket is to be used. In this embodiment, for example, adhesive 822 can be included with a backing material across its exposed surface. Upon use of the filtration device 808, the backing can be removed and the adhesive 822 can fasten or affix the assembled structure of the support body 814, filter element 818 and flexible ducting element 819 to convective thermoregulation blanket 804.

Figure 19:
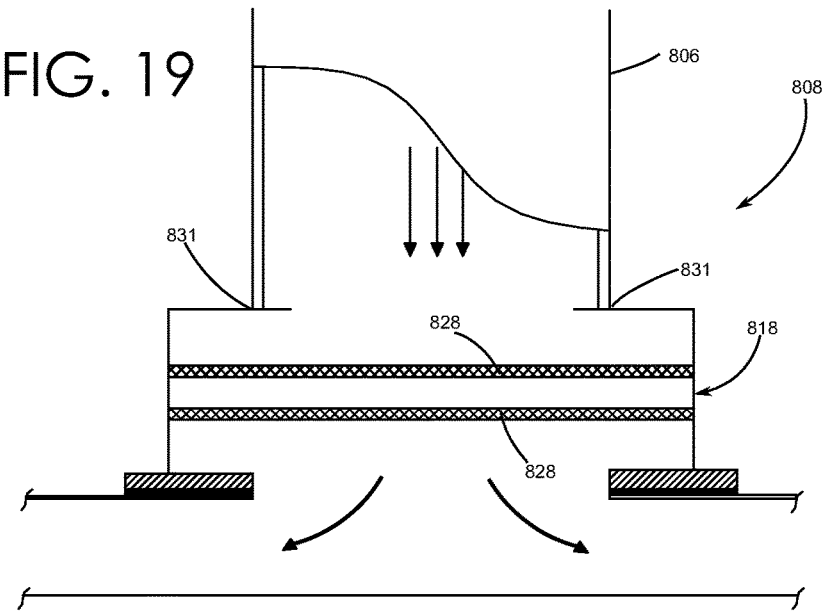
FIG. 19 is a sectional view of an alternative embodiment of the filtration device illustrated in FIG. 17.

FIG. 19 is a sectional view of an alternative embodiment of filtration device 808 of FIG. 18. In this embodiment, filter element 818 includes a plurality of filters 828 stacked into layers and spaced apart from each other. FIG. 19 illustrates two filters. However, it should be realized that any number of filters can be used. Each of the plurality of filters 828, for example, can be a different type of filter that filters different size particles. Although not particularly illustrated, filtration device 808 also can includes a sleeve coupled to the proximal end 831 of flexible ducting element 819. The sleeve cinches, fastens or affixes around hose 806 to make an airtight seal. Such affixing can be accomplished in numerous ways. For example, by adhesive or the like.

Figure 20:
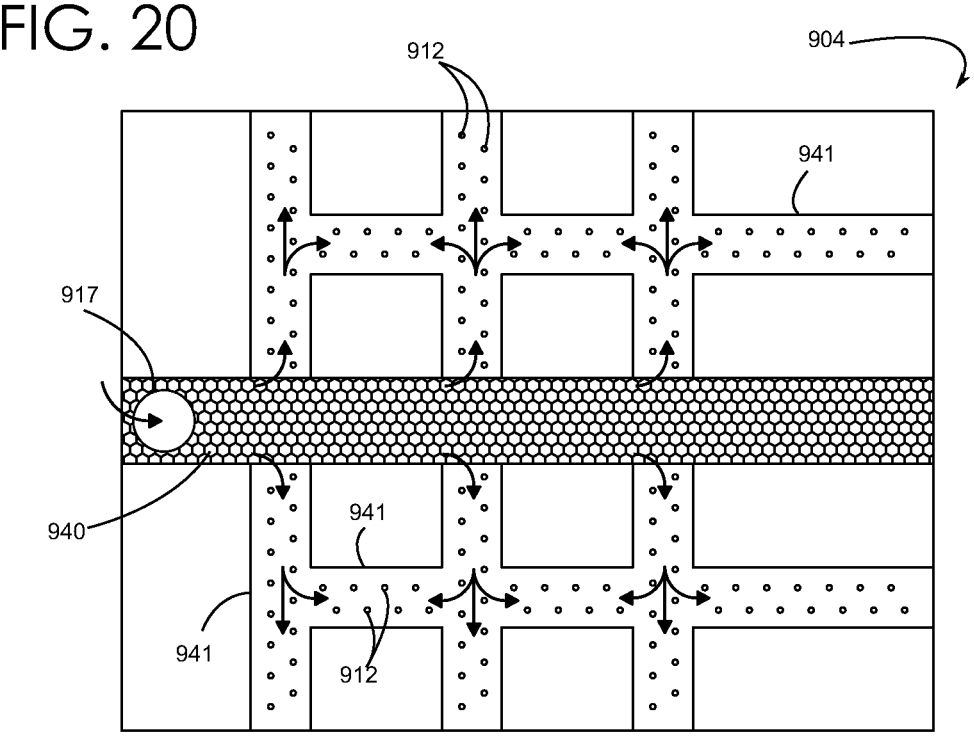
FIG. 20 illustrates a diagrammatic top view of one embodiment of a convective thermoregulation blanket.
Figure 21:
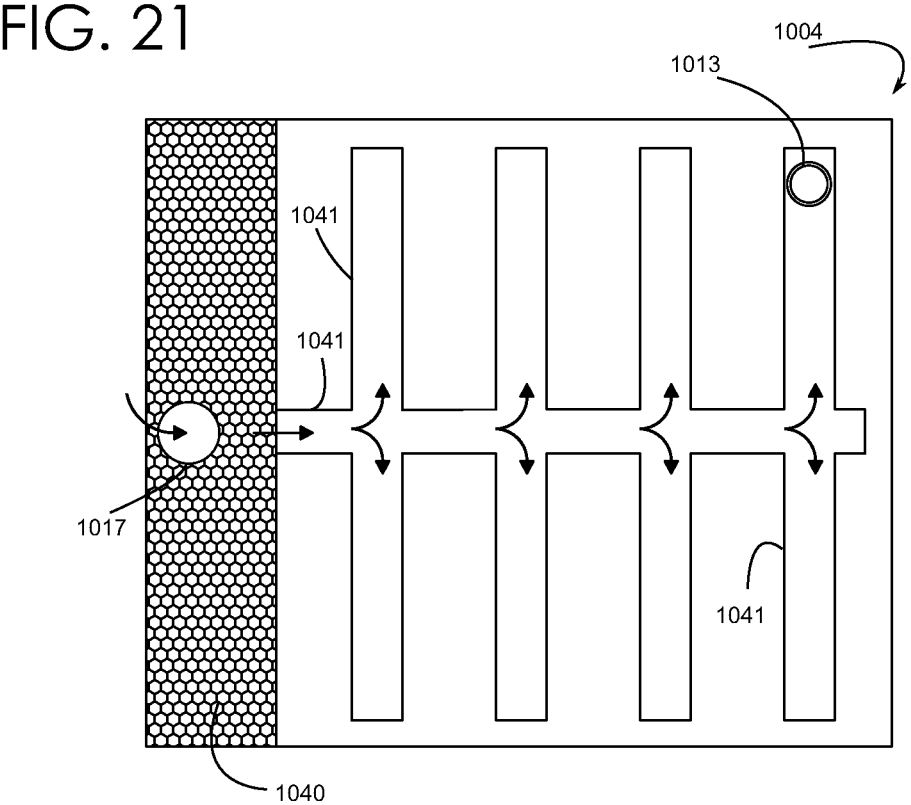
FIG. 21 illustrates a diagrammatic top view of another embodiment of a convective thermoregulation blanket.

FIGS. 20 and 21 are diagrammatic top views of embodiments of a convective thermoregulation blankets 904 and 1004. In these embodiments, an interior section or portion of blanket 904 or 1004 can be made of a filter material to maintain a clean or sterile environment when in use. As previously discussed, an interior of convective thermoregulation blanket 904, 1004 generally includes a primary distribution channel 940 or 1040. As illustrated in FIG. 20, primary distribution channel 940 is located down the center of blanket 904. However and as illustrated in FIG. 21, primary distribution channel 1040 is located at a top end of blanket 1004. Primary distribution channel 940, 1040 includes an interior surface of which an inlet opening 917 or 1017 extends between an exterior surface of the in the blanket and the interior surface of the primary distribution channel 940, 1040. At least a portion of the exterior surface of the blanket is configured to be in contact with a patient. Opening 917, 1017 is formed for receiving a supply of convective air in a hose from a blower unit and acts as the component which delivers thermal regulated convective air into primary distribution channel 940, 1040.

In one embodiment, these primary distribution channels 940, 1040 can be made of a filter material, such that upon clean or sterile convective air from a blower unit being directed into the blanket, any particles are filtered out at the primary distribution channel level. Connected to the primary distribution channel 940, 1040 is a plurality of interconnected distribution sub-channels 941, 1041 that feed clean or sterile convective air filtered in the primary distribution channel 940, 1040 to other parts of blanket 904 or 1004. As illustrated in FIG. 20, blanket 904 further includes a plurality of first outlet openings 912 extending between the exterior surface of the blanket that is in contact with a patient and interior surfaces of the interconnected distribution sub-channels 941. The plurality of first outlet openings 912 distribute filtered thermal regulated convective air onto the patient.

Therefore, air exiting the blanket 904 through first outlet openings 912 or through a single second outlet opening 1013 as illustrated in FIG. 21 is air free of harmful particles. Although blankets 904 and 1004 illustrate primary distribution channels 940 and 1040 as being made of filter material, it is possible that all distribution channels (including sub-channels) can be made of a filter material or that the entire blanket 904 or 1004 can be made of filter material.

Figure 22:
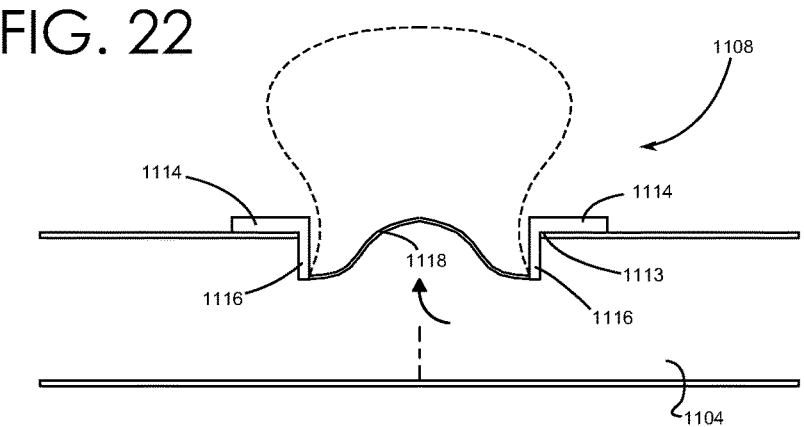
FIG. 22 illustrates a filtration device under yet another embodiment.

FIG. 22 illustrates a filtration device 1108 under another embodiment. Besides a blanket, such as blanket 1104, including an inlet port opening having a filtration device as describe in the above embodiments and a plurality of first outlet openings, such as openings 912, a blanket, such as blanket 1104, can also include an outlet port attached to a second outlet opening of a blanket, such as second outlet opening 1113. While the plurality of first outlet openings distribute thermal regulated convective air onto a patient, second outlet opening 1113 includes a filtration device 1108. As illustrated in FIG. 22, filtration device 1108 includes similar components to the filtration device designed for the inlet opening, such as a support body 1114, gasket 1126 and filter element 1118. The main difference is that the air flow through the filter element 1118 originates from the interior of the blanket 1104 and distributes to an exterior location outside the blanket 1104 to provide filtered air to a specific location or top of the blanket. For example, filtered exhaust air or waste heat could be directed to a specific location to create a clean or sterile environment outside the blanket. Filtration device 1108 also includes versatility. If necessary, second outlet opening 1113 and therefore filtration device 1108 can be used as a second filtration device in a second inlet opening. If, for example, the first filtration device is positioned in a place that is in the way of caring for the patient, the alternative second port filtration device and opening can be used to receive and filter the supply of convective air from the hose for delivering clean or sterile convective air.

Figures 1, 23:
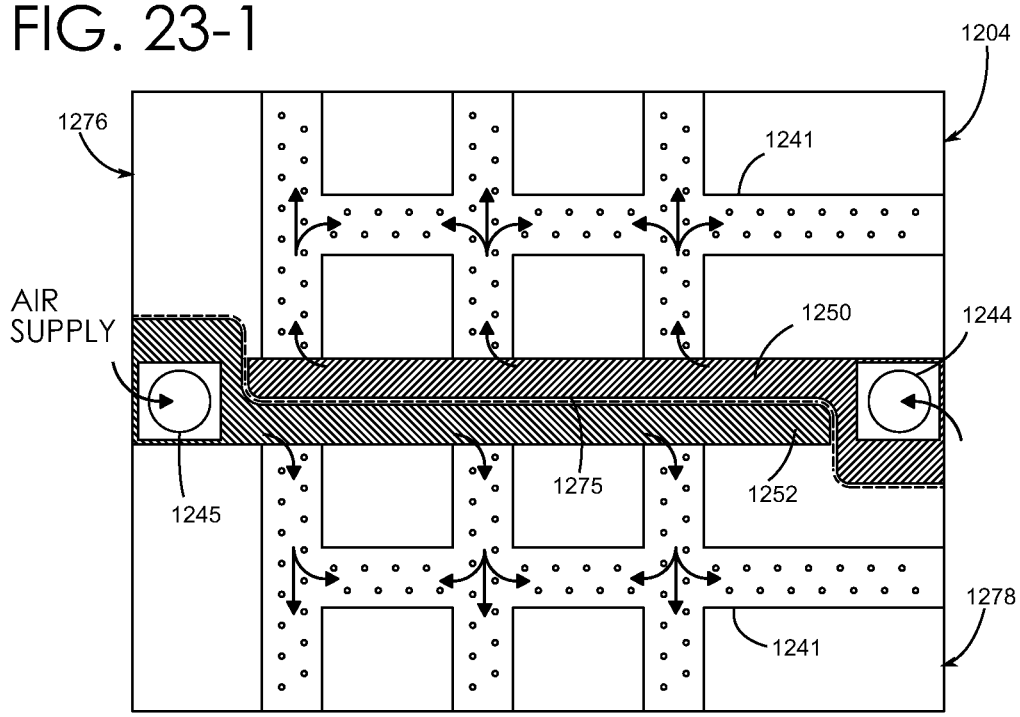
Figures 2, 23:
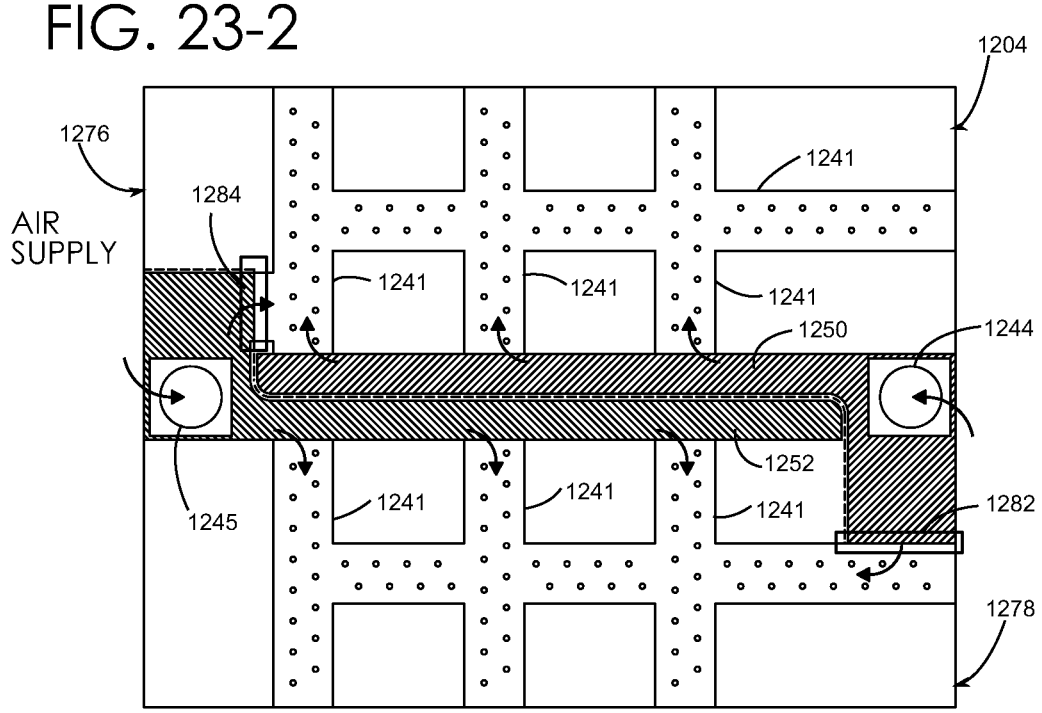
Figures 3, 23:
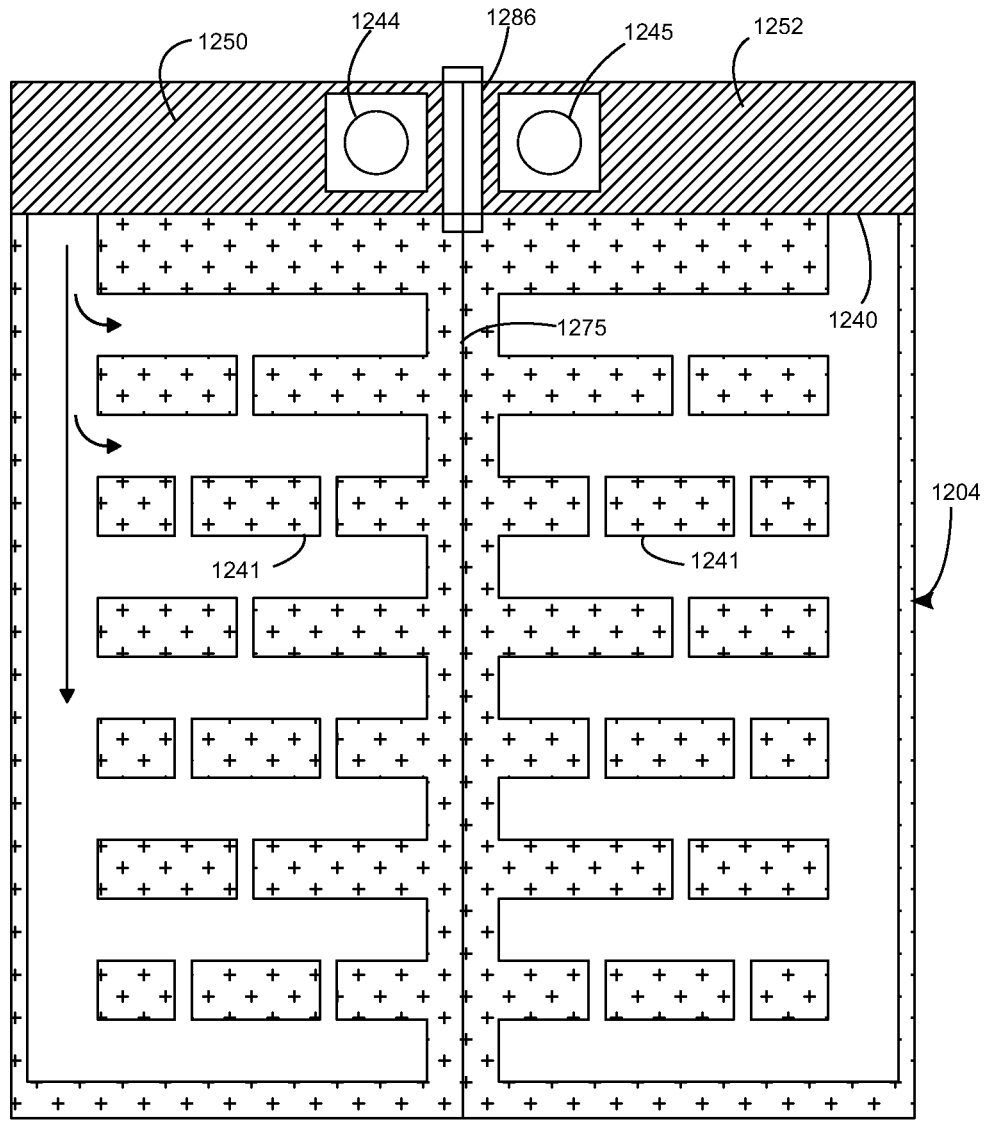

FIG. 23-1 is similar to FIG. 20 except FIG. 23-1 illustrates a diagrammatic top view of a thermoregulation blanket 1204 under an embodiment where primary distribution channel 1240 includes two chambers for accommodating two different supplies of convective air. The first chamber 1250 includes filter material for filtering a supply of convective air from a first inlet opening 1244 and the second chamber 1252 includes filter material for filtering a supply of air from a second inlet opening 1245. The first chamber 1250 is separated from the second chamber 1252 by a perforation line 1275 such that blanket 1204 can be separated into two different blankets or can remain connected to be used as a single blanket. The first chamber 1250 delivers filtered air to interconnected sub-channels 1241 in a first portion 1276 of blanket 1204 for distribution onto a patient. The second chamber 1252 delivers filtered air to interconnected sub-channels 1241 in a remaining or second portion 1278 of blanket 1204. Therefore, convective air being fed into first chamber 1250 through first inlet opening 1244 communicates only with first portion 1276 of blanket 1204 and convective air being fed into second chamber 1252 through second inlet opening 1245 communicates only with second portion 1278 of blanket 1204. Both first and second chambers 1250 and 1252 of primary distribution channel 1240 include an interior surface of which apertures 1244 and 1245 extend between an exterior surface of the blanket and the interior surfaces of first and second chambers 1250 and 1252.

FIG. 23-2 illustrates thermoregulation blanket 1204 where primary distribution channel 1240 also includes first and second chambers 1250 and 1252 made of filter material for accommodating two different supplies of convective air through first inlet opening 1244 and second inlet opening 1245. However, instead of first chamber 1250 feeding convective air only into interconnected sub-channels 1241 in a first portion 1276 of blanket 1204 and second chamber 1252 feeding convective air only into interconnected sub-channels 1241 in a remaining or second portion 1278 of blanket 1204, both first chamber 1250 and second chamber 1252 feed convective air into both first portion 1276 and second portion 1278. For example, first chamber 1250 not only feeds convective air into sub-channels 1241 located in first portion 1276, but also feeds convective air into second portion 1278 at opening 1282. Accordingly, second chamber 1252 not only feeds convective air into sub-channels 1241 located in second portion 1278, but also feeds convective air into first portion 1276 at opening 1284. Blanket 1204 still includes perforation line 1275 for separating blanket 1204 into first portion 1276 and second portion 1278. However, upon separating blanket 1204 at perforation line 1275, openings 1282 and 1284 are closed with an adhesive, clips or other types of mechanisms.

As illustrated in FIGS. 23-1 and 23-2, primary distribution channel 1240 is located through the center of blanket 1204. However, primary distribution channel 1240 can be positioned in other locations, such as on either end of blanket 1204. For example, the diagrammatical top view in FIG. 23-3 illustrates blanket 1204 where primary distribution channel 1240 is located at an end of the blanket for the distribution of filtered air to other air channels in the blanket. Channel 1240 includes filter material as is the case in FIGS. 23-1 and 23-2. In the alternative, a filtration device can be positioned at the first and second inlet openings 1244 and 1245.

In FIG. 23-3, primary distribution channel 1240 includes first and second inlet openings 1244 and 1245. Conditioned air from a blower or fan unit can be provided to primary distribution channel 1240 through either inlet opening 1244 or 1245 when the blanket 1204 is used as one large unit. The unused port would be sealed such that air could not escape. Convective air in distribution channel 1240 is fed to all interconnected sub-channels 1241 in the blanket 1204. However, blanket 1204 can be separated along a perforation line 1275 to be used as two smaller blankets with having a first chamber 1250 for distributing convective air and a second chamber 1252 for distributing convective air. When separated, the opening 1286 between first chamber 1250 and second chamber 1252 can be sealed using adhesive, clips or other types of mechanisms.

Figure 24:
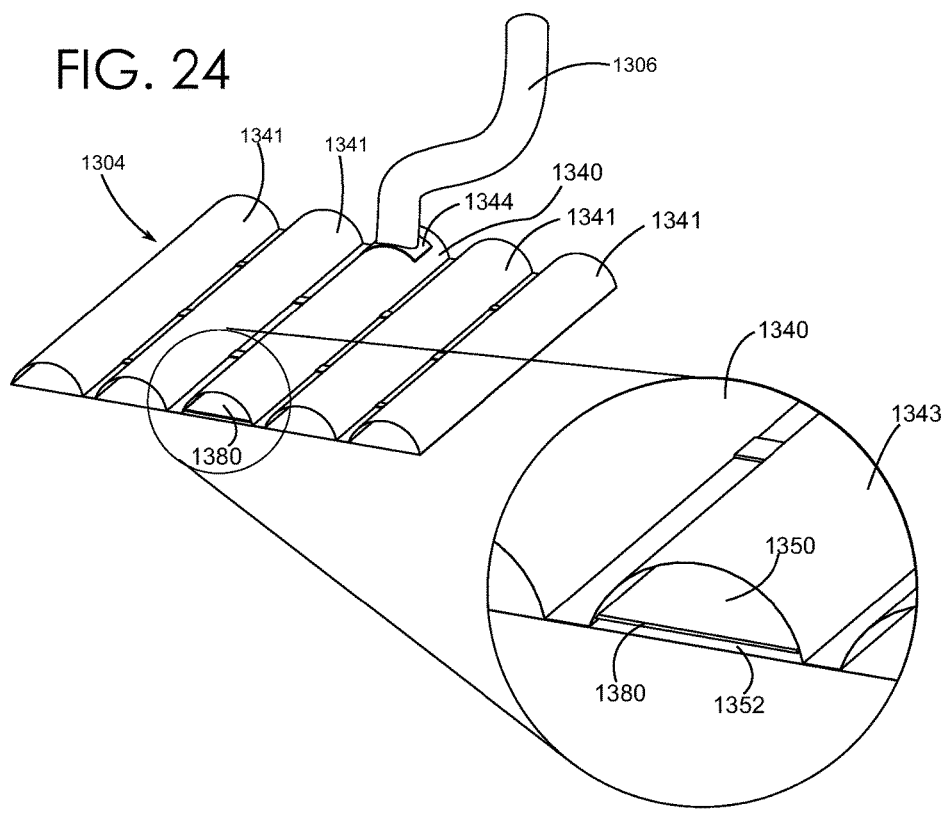
FIG. 24 illustrates a diagrammatic perspective view of another embodiment of a convective thermoregulation blanket.

FIG. 24 illustrates a perspective view of a convective thermoregulation blanket 1304. Blanket 1304 includes a plurality of longitudinal interconnected sub-channels 1341 and a primary distribution channel 1340 having a top layer which is impervious to airflow. In particular, each channel 1341 and 1340 includes a poly top layer that is impervious to airflow. The central most primary distribution channel 1340 is at least partially made of a filter material and includes an inlet opening an inlet port 1344 for mating with an incoming air supply, such as a supply of thermal regulated convective air from a hose 1306 coupled to a blower or fan unit. As illustrated in more detail in FIG. 24, primary distribution channel 1340 includes two chambers separated by filter material 1380. The upper chamber 1350 includes an unfiltered air chamber 1350 and the lower chamber 1352 includes filtered air chamber 1352. Upper chamber 1350 is in fluidic communication with the inlet opening 1344 to receive the supply of convective air stream from the blower or fan unit. Such a supply of air stream is contaminated with particulate unsafe to the surgical or wound site or sterile environment. Lower chamber 1352 is in fluidic communication with the other sub-channels 13541 of the thermoregulation blanket 1304. Filter material 1380 is completely sealed to the impervious top layer so that none of the unfiltered air in upper chamber 1350 can seep into the filtered air in lower chamber 1352.

In FIG. 24, upper chamber 1350 is located above lower chamber 1352. Upon the upper chamber 1350 attaining a particular air pressure, the inlet supply of air from hose 1306 filters down through the filter material 1380 into the lower chamber 1352. Filtered air is then distributed to the other air sub-channels 1341 in the thermoregulation blanket 1304. Although not clearly illustrated in FIG. 24, thermoregulation blanket 1304 includes perforations or, first outlet openings or other means to distribute filtered airflow out the bottom layer of the blanket 1304 such that the filtered air can exit to warm or cool the patient. Filtered air enters lower chamber 1352 and inflates all other channels 1341 of the blanket 1304 for even distribution of filtered air throughout the blanket and through the perforations or other means to the patient. The bottom layer of the blanket 1304 can be made of a woven or non-woven material. In addition, although FIG. 24 illustrates blanket 1304 that is essentially similar to the blanket 904 in FIG. 20, it is possible for the configuration of upper chamber 1350 being located above and separated by a filter 1380 from lower chamber 1352 to be used in the embodiments illustrated in FIGS. 23-1 through 23-3. In such a configuration, both chambers 1250 and 1252 include upper and lower chambers 1350 and 1352.

Figure 25:
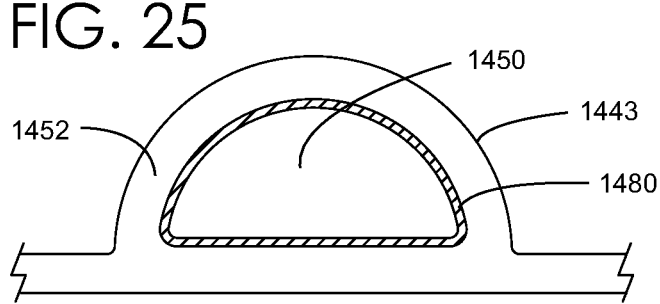
FIG. 25 illustrates a sectional view of another embodiment of a primary distribution channel.

FIG. 25 illustrates a side sectional view of an alternative embodiment of a primary distribution channel 1440 under another embodiment. Like FIG. 24, channel 1440 includes two chambers separated by filter material 1480 and includes an inner chamber 1450 of unfiltered air and an outer chamber 1452 of filtered air. Instead of air chamber 1450 containing unfiltered air being located above chamber 1452 containing filtered air, inner chamber 1450 is located internal to outer chamber 1452 and is in communication with a supply of convective air from the blower or fan unit. Therefore, a sleeve of filter material 1480 encloses inner chamber 1450 and outer chamber 1452 is located between the impervious interior surface of channel 1440 and the filter material 1480. Like the embodiment described above, air in outer chamber 1452 is in communication with all other channels of the thermoregulation blanket such that even distribution of filtered air through out the blanket and through the perforations to a patient is accomplished. In addition, it is possible for the configuration of inner chamber 1450 being internal to and separated by a filter 1480 from outer chamber 1452 can be used in the embodiments illustrated in FIGS. 23-1 through 23-3. In such a configuration, both chambers 1250 and 1252 include inner and outer chambers 1450 and 1452. In yet another embodiment, only one of chambers 1250 and 1252 can include either upper chamber 1350 and lower chamber 1352 or inner chamber 1450 and outer chamber 1452. In such a configuration, one of chambers 1250 and 1252 filters convective air, while the other of the chambers does not.

Figure 26:
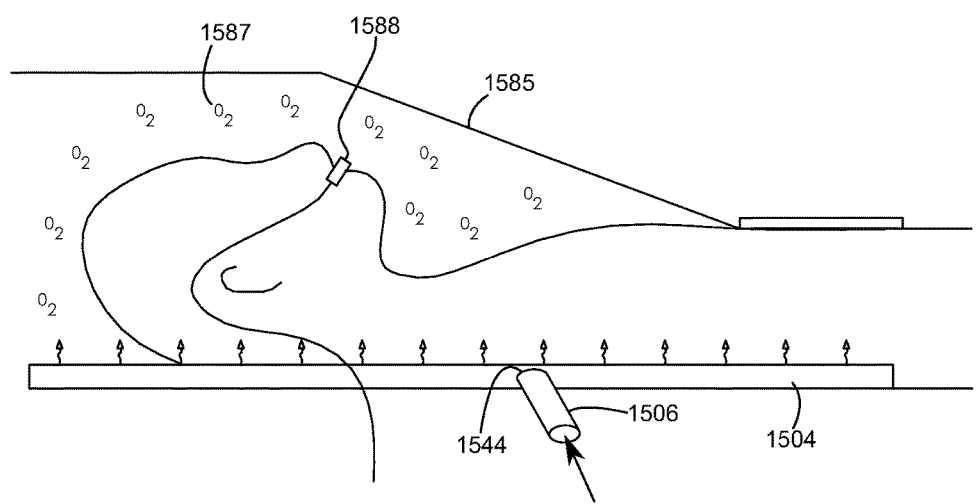
FIG. 26 is a diagrammatic side view of a patient laying on top of another embodiment of a thermoregulation blanket.

FIG. 26 illustrates yet another convective thermoregulation blanket 1504 where a patient lays on top of the blanket and perforations are made in the top layer of the blanket. Such internal structure of blanket 1504 can be similar in scope to any of the concepts presented above including an inlet opening, which receives a supply of thermoregulated convective air from a hose 1506. In addition, blanket 1504 provides further benefits than just thermal regulation of air. It also provides regulation of a gas concentration around a patient when their breathing is supplemented with higher concentrations of oxygen by a facemask, nasal cannula, or another supplemental oxygen source 1588. As described above, in oxygen rich environments, as would occur when a patient's head is covered by a surgical drape 1585 as illustrated in FIG. 26, a first supply of gas 1587, such as oxygen and other flammable or combustible gases from the supply source, such as nasal cannula 1588, surgical prep solution or vapor, can become entrapped around the surgical site or patient. The higher concentration of the first supply of gas 1587 increases the risk of surgical fires, especially when a heat or ignition source such as an electrocautery unit or laser is introduced in this environment. By providing a second supply of gas from filtering convective air in a convective thermoregulation blanket, varying gas concentrations that are low in oxygen, inert, or noncombustible such as ambient air, nitrogen, carbon dioxide, or helium, airflow exiting the blanket can dilute and displace (wash out) gases that create or support combustion such as flammable gases, accelerants, or oxidizers. Creating a local clean or sterile environment that can also create varying oxygen concentrations around a surgical site and patient will significantly decrease the risk of surgical fires near and around the patient and surgical environment.

In the alternative, blanket 1504 could be used as a surgical or head drape in order to deliver filtered thermal regulated air to the surgical site or the patient for regulating patient body temperature and also washing away high concentrations of oxygen or other harmful and flammable vapors. In yet another alternative, the thermoregulation blanket could be used in the form of a bed, mattress, or on an instrument tray or table.

Figure 27:
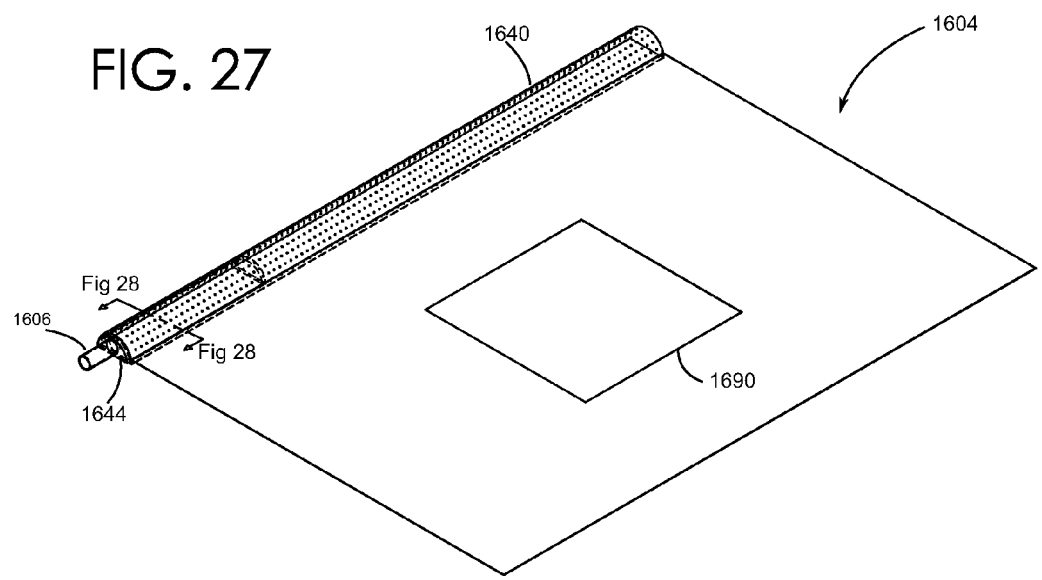
FIG. 27 is a perspective view of a convective thermoregulation blanket under another embodiment.
Figure 28:
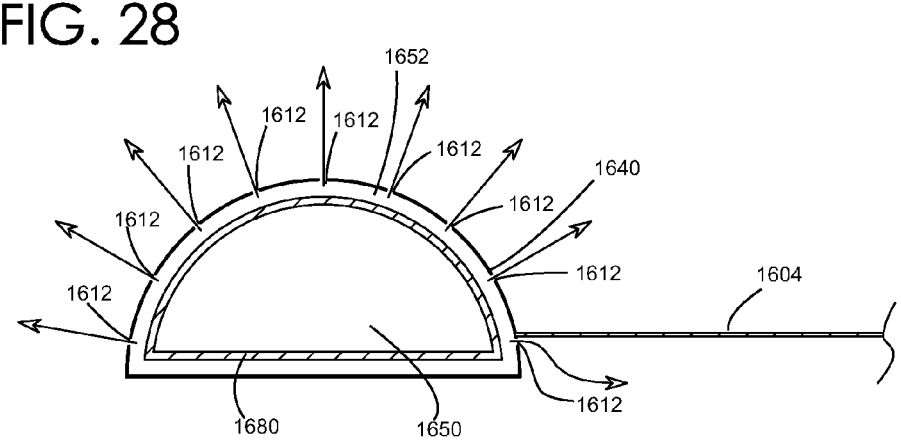
FIG. 28 is a diagrammatic sectional view of the primary distribution channel illustrated in FIG. 27.

FIG. 27 illustrates a perspective view of a thermoregulation blanket 1604 used as a patient warming device or surgical site drape to deliver filtered thermal regulated air to not only the patient, but also to a surgical site so that any contaminants located in proximity of the surgical site can be carried away. Thermoregulation blanket 1604 includes an opening 1690 for a surgical site and a primary distribution channel 1640 having an inlet opening 1644 that receives a supply of convective air from a hose 1606. As illustrated in FIG. 28, convective air from hose 1606 is received in an inner chamber 1650 and is filtered by a filter material 1680 surrounding inner chamber 1650. Outer chamber 1652 includes filtered convective air and is defined between filter material 1680 and the interior surface of primary distribution channel 1640.

Primary distribution channel 1640 includes a plurality of apertures 1612 for distributing convective air to the surrounding environment. In FIGS. 27 and 28, most of the apertures 1612 distribute air on top of blanket 1604 to provide a directional flow of filtered air over the sterile surgical site. This flow of filtered air carries any contaminants located in the surgical environment away to maintain a clean or sterile environment. However, at least one of the apertures 1612 is located below an exterior surface of blanket 1604 and thereby distributes filtered convective air to the patient's body for controlling patient temperature.

Figures 1, 29:
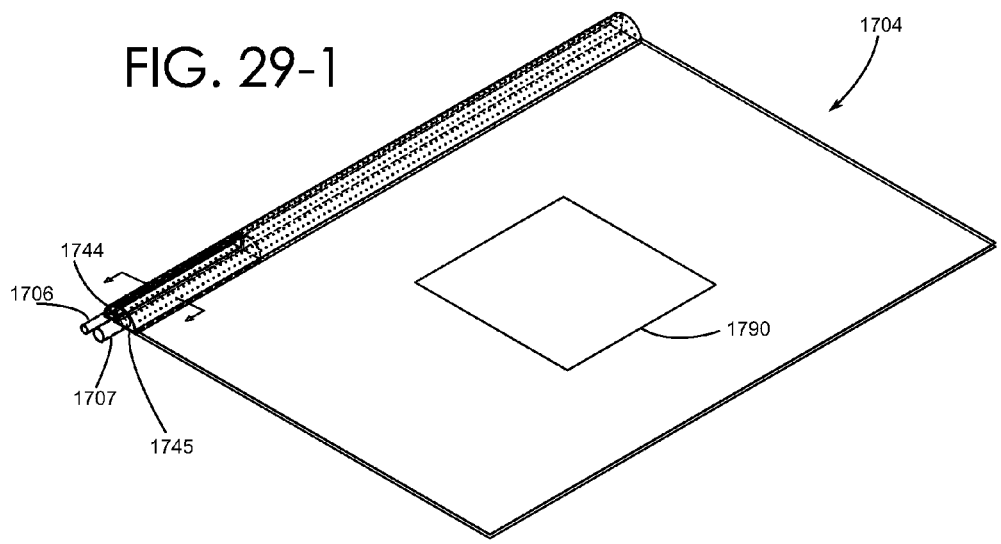
Figures 2, 29:
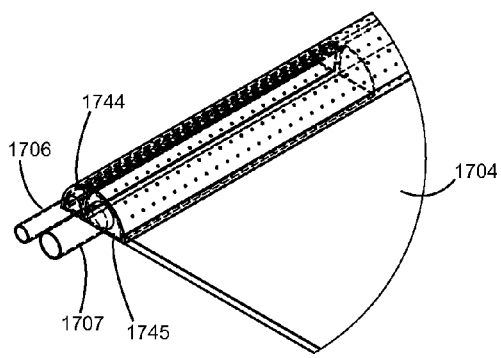
Figures 3, 29:
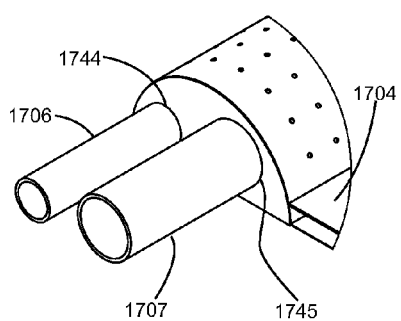
Figure 30:
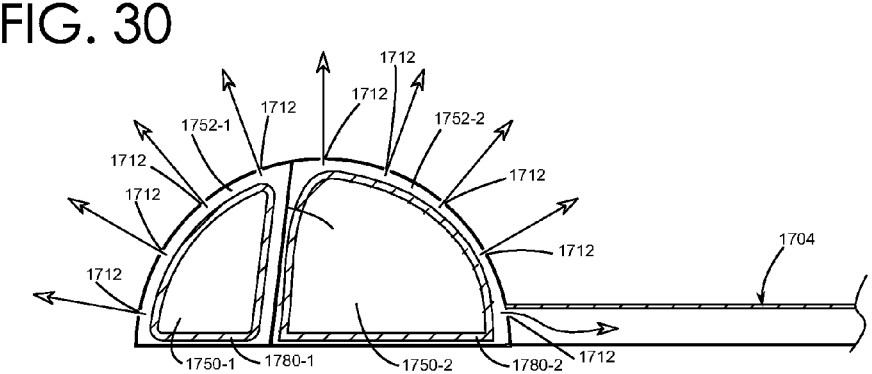
FIG. 30 is a diagrammatic sectional view of the primary distribution channel illustrated in FIGS. 29-1 through 29-3.

FIGS. 29-1, 29-2 and 29-3 illustrate perspective views of another embodiment of a thermoregulation blanket 1704 used as a patient warming device and surgical site drape to deliver filtered thermal regulated air to not only the patient, but also to a surgical site so that any contaminants located in proximity of the surgical site can be carried away. Thermoregulation blanket 1704 includes an opening 1790 for a surgical site and a primary distribution channel 1740 having a pair of inlet openings 1744 and 1745 that receive a supply of convective air through hoses 1706 and 1707. The surgical site defined by opening 1790 includes a first supply of air that can include airborne contaminants, such as particulate and harmful biological contaminates. As illustrated in FIG. 30, convective air from hose 1706 is received in a first inner chamber 1750-1 and is filtered by a filter material 1780-1 surrounding first inner chamber 1750-1. First outer chamber 1752-1 includes filtered convective air and is defined between filter material 1780-1 and a portion of the interior surface of primary distribution channel 1740. Convective air from hose 1707 is received in a second inner chamber 1750-2 and is filtered by a filter material 1780-2 surrounding second inner chamber 1750-2. Second outer chamber 1752-2 includes filtered convective air and is defined between filter material 1780-2 and a portion of the interior surface of primary distribution channel 1740. First inner and outer chambers 1750-1 and 1752-1 and second inner and outer chambers 1750-2 and 1752-2 are separated by an impermeable barrier 1792.

Primary distribution channel 1740 includes a plurality of apertures 1712 for distributing convective air to the surrounding environment. In FIGS. 29 and 30, most of the apertures 1712 distribute air on top of blanket 1704 to thereby provide a second supply of filtered air or a directional flow of filtered air over the sterile surgical site. This flow of filtered air or second supply of air carries any contaminants located in the surgical environment away to maintain a sterile environment. However, at least one of the apertures 1712 distributes convective air within blanket 1704 and thereby distributes filtered convective air to the patient's body for controlling patient temperature.

In addition, the pair of inlet openings 1744 and 1745 can receive different temperatures or different types of convective air or gas. For example, inlet opening 1744 could receive cool air while inlet opening 1745 can receive warm air. In another example, inlet opening 1744 could receive one type of gas while inlet opening 1745 could receive a different type of gas. However, in yet another example, inlet opening 1744 could receive the same temperature and same type of gas as inlet opening 1745.

FIGS. 31 and 32 illustrate sectional views of additional embodiments of a thermoregulation blanket 1804 and 1904 used as patient warming devices and surgical site drapes to deliver filtered thermal regulated air to not only the patient 1896, 1996, but also to a surgical site so that any contaminants located in proximity of the surgical site can be carried away. Like the blankets illustrated in FIGS. 27 and 29, blankets 1804 and 1904 include openings 1890, 1990 for a surgical site. Blankets 1804 and 1904 can include any of the above the embodiments in terms of filtration devices incorporated into inlet openings or primary distribution channels including or made of filter material.

The perimeter of openings 1890 and 1990 not only include an adhesive 1893, 1993 to seal the openings 1890 and 1990 to the patient, but also include inwardly facing surface(s) 1891 and 1991. Inwardly facing surface(s) 1891 and 1991 including outlet openings that are in fluidic communication with filtered air in blankets 1804 and 1904. This filtered air exits through the outlet openings in inwardly facing surface(s) and carry harmful contaminants up or away from the sterile environment or surgical site. In combination, filter air exits through perforations in the bottom of blankets 1804 and 1904 to thermally regulate the temperature of patient 1896 or 1996. In FIG. 32, blanket 1904 includes two distinct chambers 1950 and 1952, which are not in fluidic communication with each other. First chamber 1950 delivers filtered air to the sterile environment or surgical site to carry contaminants away, while second chamber 1952 delivers filtered air to the thermally regulate patient 1996.

FIG. 33 illustrates a perspective view of an alternative embodiment of a convective thermoregulation blanket 1904. Blanket 1904 includes at least two distribution plenums 1967-1 and 1967-2. As illustrated in the sectional view of FIG. 33, distribution plenums 1967-1 and 1967-2 include a plurality of apertures 1912, located on exterior surfaces 1920-1 and 1920-2, for distributing convective air or other gases to the surrounding environment. Blanket 1904 additionally includes a layer 1966, which captures or surrounds the air or gas distributed by blanket 1904 from apertures 1912 from one or more of surfaces 1920-1 and 1920-2. Layer 1966 can, for example, confine warm air or other gas distributed from the apertures 1912 located on the upper surface 1920-1 of blanket 1904 to the space 1970 between layer 1966 and the exterior surface 1920-1 of the convective regulation blanket. Layer 1968 can consist of a filter element, a gas impermeable layer, such as a plastic film, a combination of filter material and an impermeable layer, or a gas permeable layer, such as a porous woven or nonwoven. Other configurations of air distribution channels are considered. For example a single distribution plenum, or a plurality of distribution channels. In addition, other embodiments where apertures for distributing convective air are located only on the top surface of the blanket, only of the bottom surface of the blanket, or only partially covering the upper, lower, or both surfaces of the blanket are considered.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. For example, the surface area of the filter element can be of varying sizes and the inlet/outlet ports can allow the insertion of a distal end of a blower hose of varying sizes.

What is claimed is:

1. A convective thermoregulation blanket comprising:
   an exterior surface, wherein a portion of the exterior surface is configured to be in contact with a patient;
   an interior having a length and a width;
   a primary distribution channel having an interior surface and being located in the interior of the convective thermoregulation blanket and extending across an entirety of the length or the width of the interior of the convective thermoregulation blanket;
   at least one compartment having an interior surface and being located in the interior of the convective thermoregulation blanket, wherein the at least one compartment intersects with the primary distribution channel in at least one intersecting area and wherein the at least one intersecting area provides fluidic communication between the primary distribution channel and the at least one compartment, the at least one compartment including a plurality interconnected distribution channels; and
   a first inlet opening extending between the exterior surface of the convective thermoregulation blanket and the interior surface of the primary distribution channel to deliver unfiltered thermal regulated convective air into an entirety of the primary distribution channel;

wherein each intersecting area between the primary distribution channel and the at least one compartment comprises filter material that prevents harmful particles in the unfiltered thermal regulated convective air from passing from the primary distribution channel into the at least one compartment;

wherein the contaminate free air in the at least one compartment is distributed throughout the at least one compartment with the plurality of interconnected distribution channels.

2. The convective thermoregulation blanket of claim 1, further comprising at least one outlet opening extending between the exterior surface of the convective thermoregulation blanket and an interior surface of the at least one compartment.

3. The convective thermoregulation blanket of claim 2, further comprising a filter coupled to and extending across the at least one outlet opening.

4. The convective regulation blanket of claim 2, wherein the at least one outlet opening is located on the portion of the exterior surface of the convective thermoregulation blanket that is not configured to be in contact with the patient.

5. The convective thermoregulation blanket of claim 1, further comprising a second inlet opening extending between the exterior surface of the convective thermoregulation blanket and the interior surface of the primary distribution channel to deliver thermal regulated convective air into the primary distribution channel, the second inlet opening allowing the convective thermoregulation blanket to be separated into a first convective thermoregulation blanket portion and a second convective thermoregulation blanket portion.

6. The convective thermoregulation blanket of claim 1, further comprising a surgical site opening in the thermoregulation blanket, the surgical site opening including outlet openings on a surface of the convective thermoregulation blanket for providing a filtered airflow to the surgical site so as to carry away airborne contaminants in proximity to the surgical site.

7. The convective regulation blanket of claim 1, further comprising a sealing component that seals a distal end of a hose that supplies the first inlet opening with the thermal regulated convective air.

8. A convective thermoregulation blanket comprising:
an interior having a length and a width;
an exterior surface having a portion configured to be in contact with a patient;
an internal primary compartment located in the interior and having a first chamber and a second chamber, wherein the first chamber is separated from the second chamber at least partially by filter material that filters harmful airborne contaminants, wherein the internal primary compartment extends across an entirety of the length or the width of the interior of the convective thermoregulation blanket;
at least one internal secondary compartment located in the interior and being separate from the internal primary compartment, wherein the at least one internal secondary compartment intersects with the second chamber of the internal primary compartment in at least one intersecting area, the at least one intersecting area providing fluidic communication between the second chamber and the at least one internal secondary compartment;
an inlet opening extending between the exterior surface and an interior surface of the first chamber of the internal primary compartment and configured to receive a supply of unfiltered thermal regulated convective air for distributing into the first chamber of the internal primary compartment; and
at least one outlet opening extending between the exterior surface and an interior surface of the at least one internal secondary compartment;
wherein the supply of unfiltered thermal regulated convective air located in an entirety of the first chamber of the internal primary compartment is filtered by the filter material so that contaminate free air flows into the second chamber of the internal primary compartment; and
wherein the contaminate free air in the second chamber of the internal primary compartment enters into the at least one internal secondary compartment through the at least one intersecting area and exits out of the at least one outlet opening;
wherein the at least one internal secondary compartment comprises a plurality interconnected distribution channels, wherein the contaminate free air in the second chamber of the internal primary compartment is provided to the plurality of interconnected distribution channels.

9. The convective thermoregulation blanket of claim 8, further comprising a sealing component that seals a distal end of a hose that supplies the inlet opening with the supply of thermal regulated convective air.

10. The convective thermoregulation blanket of claim 9, wherein the sealing component comprises a flexible ducting element having a proximal end and a distal end, the proximal end of the flexible ducting element receiving the distal end of the hose and the distal end of the flexible ducting element being coupled to a support body that surrounds the inlet opening.

11. The convective thermoregulation blanket of claim 8, wherein a filter is coupled to and extends across the inlet opening.

12. The convective thermoregulation blanket of claim 8, wherein the first chamber of the internal primary compartment is located internal to the second chamber of the internal primary compartment.

13. The convective regulation blanket of claim 8, wherein the at least one outlet opening is located on the portion of the exterior surface of the convective thermoregulation blanket that is not configured to be in contact with the patient.

14. A convective thermoregulation blanket comprising:
an exterior surface, wherein a portion of the exterior surface is configured to be in contact with a patient;
an interior having a length and a width;
an inlet opening configured to receive a supply of unfiltered thermal regulated convective air;
a primary channel located in the interior of the convective thermoregulation blanket, in fluidic communication with the inlet opening and extending an entirety of the length or the width of the interior of the convective thermoregulation blanket;
at least one chamber located in the interior of the convective thermoregulation blanket and outside of the primary channel, wherein the at least one chamber intersects with the primary channel in at least one intersecting area and wherein the at least one intersecting area provides fluidic communication between the primary channel and the at least one chamber; and at least one outlet opening extending between the exterior surface of the convective thermoregulation blanket and an interior surface of the at least one chamber, wherein the at least one outlet opening is located on the portion of the exterior surface of the convective thermoregulation blanket that is not configured to be in contact with the patient; and wherein each intersecting area comprises a filter material that filters harmful airborne contaminants in the supply of unfiltered thermal regulated convective air located in an entirety of the primary channel and provides the contaminate free air to the at least one chamber so that contaminate free thermal regulated convective air exits through the at least one outlet opening;

wherein the at least one chamber comprises a plurality of interconnected distribution channels located internal to the convective thermoregulation blanket, wherein the filter material provides the contaminate free air to the plurality of interconnected distribution channels.

15. The convective thermoregulation blanket of claim 14, wherein the at least one outlet opening extends between the exterior surface and an interior surface of each of the plurality of interconnected distribution channels.

16. The convective thermoregulation blanket of claim 14, further comprising a surgical site opening in the convective thermoregulation blanket, the surgical site opening including openings on a surface of the convective thermoregulation blanket for providing filtered air to the surgical site so as to carry away airborne contaminants in proximity to the surgical site.

17. The convective regulation blanket of claim 14, further comprising a sealing component that seals a distal end of a hose that supplies the inlet opening with the thermal regulated convective air.

18. The convective regulation blanket of claim 14, wherein the primary channel extends across an entirety of at least one dimension of the convective thermoregulation blanket.

19. A convective thermoregulation blanket comprising:
an exterior surface, wherein a portion of the exterior surface is configured to be in contact with a patient;
an interior having a length and a width;
a primary distribution channel having an interior surface and being located in the interior of the convective thermoregulation blanket and extending across an entirety of the length or the width of the interior of the convective thermoregulation blanket;
at least one compartment having an interior surface and being located in the interior of the convective thermoregulation blanket, wherein the at least one compartment intersects with the primary distribution channel in at least one intersecting area and wherein the at least one intersecting area provides fluidic communication between the primary distribution channel and the at least one compartment; and
a first inlet opening extending between the exterior surface of the convective thermoregulation blanket and the interior surface of the primary distribution channel to deliver unfiltered thermal regulated convective air into an entirety of the primary distribution channel; and
a second inlet opening extending between the exterior surface of the convective thermoregulation blanket and the interior surface of the primary distribution channel to deliver thermal regulated convective air into the primary distribution channel, the second inlet opening allowing the convective thermoregulation blanket to become at least a first convective thermoregulation blanket portion and a second convective thermoregulation blanket portion;
wherein each intersecting area between the primary distribution channel and the at least one compartment comprises filter material that prevents harmful particles in the unfiltered thermal regulated convective air from passing from the primary distribution channel into the at least one compartment.

* * * * *